United States Patent
Lueken et al.

(10) Patent No.: US 10,017,443 B2
(45) Date of Patent: Jul. 10, 2018

(54) OPTIMIZED SEPARATION TECHNIQUE FOR WORK-UP OF HOMOGENEOUSLY CATALYSED HYDROFORMYLATION MIXTURES

(71) Applicants: Hans-Gerd Lueken, Marl (DE); Bart Hamers, Horst (NL); Dirk Fridag, Haltern am See (DE); Robert Franke, Marl (DE); Markus Priske, Mobile, AL (US); Dieter Hess, Marl (DE); Marc Becker, Dortmund (DE); Markus Rudek, Bonn (DE)

(72) Inventors: Hans-Gerd Lueken, Marl (DE); Bart Hamers, Horst (NL); Dirk Fridag, Haltern am See (DE); Robert Franke, Marl (DE); Markus Priske, Mobile, AL (US); Dieter Hess, Marl (DE); Marc Becker, Dortmund (DE); Markus Rudek, Bonn (DE)

(73) Assignee: Evonik Degussa GmbH, Essen (DE)

( * ) Notice: Subject to any disclaimer, the term of this patent is extended or adjusted under 35 U.S.C. 154(b) by 247 days.

(21) Appl. No.: 14/770,525

(22) PCT Filed: Feb. 13, 2014

(86) PCT No.: PCT/EP2014/052779
§ 371 (c)(1),
(2) Date: Aug. 26, 2015

(87) PCT Pub. No.: WO2014/131623
PCT Pub. Date: Sep. 4, 2014

(65) Prior Publication Data
US 2016/0002136 A1 Jan. 7, 2016

(30) Foreign Application Priority Data
Feb. 26, 2013 (DE) .................. 10 2013 203 117

(51) Int. Cl.
| | |
|---|---|
| C07C 45/78 | (2006.01) |
| C07C 29/16 | (2006.01) |
| C07C 45/50 | (2006.01) |
| C07C 45/82 | (2006.01) |
| B01D 61/02 | (2006.01) |
| B01J 19/00 | (2006.01) |
| C07C 45/81 | (2006.01) |
| B01J 31/18 | (2006.01) |

(52) U.S. Cl.
CPC .......... *C07C 45/786* (2013.01); *B01D 61/02* (2013.01); *B01J 19/00* (2013.01); *C07C 29/16* (2013.01); *C07C 45/50* (2013.01); *C07C 45/81* (2013.01); *C07C 45/82* (2013.01); *B01D 2311/25* (2013.01); *B01D 2317/025* (2013.01); *B01D 2325/30* (2013.01); *B01D 2325/38* (2013.01); *B01J 31/185* (2013.01); *B01J 2231/321* (2013.01); *B01J 2531/822* (2013.01)

(58) Field of Classification Search
CPC .............. B01D 61/02; B01D 2317/025; B01D 2325/30; B01D 2325/38; B01D 2311/25; B01J 31/185; B01J 19/00; B01J 2231/321; B01J 2531/822; C07C 29/16; C07C 45/786; C07C 45/50; C07C 45/81
See application file for complete search history.

(56) References Cited

U.S. PATENT DOCUMENTS

| | | | |
|---|---|---|---|
| 4,447,661 A | 5/1984 | Hoshiyama et al. | |
| 5,180,854 A * | 1/1993 | Abatjoglou | .............. C07C 45/50 568/451 |
| 5,817,884 A | 10/1998 | Bahrmann | |
| 5,877,358 A * | 3/1999 | Garton | .................. C07C 29/141 568/882 |
| 6,291,717 B1 * | 9/2001 | Takai | ..................... B01J 31/185 568/451 |

(Continued)

FOREIGN PATENT DOCUMENTS

| | | |
|---|---|---|
| DE | 10 2004 033 410 A1 | 9/2005 |
| DE | 10 2005 046 250 A1 | 3/2007 |

(Continued)

OTHER PUBLICATIONS

German Search Report dated Sep. 12, 2013 in Patent Application No. 10 2013 203 117.3 (with English translation of categories of cited documents).

(Continued)

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

The invention relates to a method for producing alcohols by homogeneously catalyzed hydroformylation of olefins to aldehydes and subsequent hydration of the aldehydes. The invention further relates to a system for carrying out the method. The main focus is on the separation technique for work-up of the hydroformylation mixture. The problem addressed by the invention is that specifying a work-up method for hydroformylation mixtures that utilizes the specific advantages of known separation technologies but at the same time largely avoids the specific disadvantages of said separation technologies. The most important objective is to create a catalyst separation system that is as complete and at the same time conservative as possible and that operates in a technically reliable manner and entails low investment and operating costs. The method should be unrestrictedly suitable for processing the reaction output from oxo systems in "world scale" format. The problem is solved by combining membrane separation units and a thermal separation unit, the thermal separation unit being operated in such a manner that 80% to 98% of the mass introduced with the product stream into the thermal separation unit exits the thermal separation unit again as a head product.

14 Claims, 16 Drawing Sheets

(56) References Cited

U.S. PATENT DOCUMENTS

| | | | |
|---|---|---|---|
| 6,482,992 | B2 | 11/2002 | Scholz et al. |
| 6,500,991 | B2 * | 12/2002 | Wiese .................. B01J 31/185 |
| | | | 568/451 |
| 7,154,012 | B2 | 12/2006 | Lueken et al. |
| 7,179,947 | B2 | 2/2007 | Lueken et al. |
| 8,129,571 | B2 | 3/2012 | Lueken et al. |
| 8,138,379 | B2 | 3/2012 | Lueken et al. |
| 8,226,829 | B2 | 7/2012 | Wiese et al. |
| 8,389,774 | B2 | 3/2013 | Becker et al. |
| 8,415,520 | B2 | 4/2013 | Winterberg et al. |
| 8,748,643 | B2 | 6/2014 | Priske et al. |
| 8,969,628 | B2 | 3/2015 | Priske et al. |
| 9,149,780 | B2 | 10/2015 | Hamers et al. |
| 2006/0128998 | A1 | 6/2006 | Lueken et al. |
| 2008/0251456 | A1 * | 10/2008 | Wiese .................. B01D 53/22 |
| | | | 210/637 |
| 2012/0035382 | A1 | 2/2012 | Priske et al. |
| 2015/0018576 | A1 | 1/2015 | Baumgarten et al. |
| 2015/0299079 | A1 | 10/2015 | Fridag et al. |

FOREIGN PATENT DOCUMENTS

| | | |
|---|---|---|
| DE | 10 2008 007 080 A1 | 8/2009 |
| EP | 1 674 441 A1 | 6/2006 |
| EP | 1 931 472 B1 | 1/2009 |
| JP | 10-59890 A | 3/1998 |
| JP | 2005-529916 A | 10/2005 |
| JP | 2009-513320 A | 4/2009 |
| JP | 2016-160745 A | 9/2016 |
| WO | WO 03/095406 A1 | 11/2003 |
| WO | WO 2010/097428 A1 | 9/2010 |
| WO | WO 2014/183952 A1 | 11/2014 |
| WO | WO 2015/014741 A1 | 2/2015 |
| WO | WO 2015/058919 A1 | 4/2015 |

OTHER PUBLICATIONS

U.S. Appl. No. 14/380,647, filed Aug. 22, 2014, 2015/0018576, Baumgarten, et al.
U.S. Appl. No. 14/890,821, filed Nov. 12, 2015, Priske, et al.
U.S. Appl. No. 14/653,717, filed Jun. 18, 2015, 2015/0299079, Fridag, et al.
International Search Report dated Jun. 3, 2014 in PCT/EP2014/052779.
Yu Huang, et al., "Low-Energy Distillation-Membrane Separation Process" Industrial & Engineering Chemistry Research, vol. 49, No. 8, XP002657719, 2010, pp. 3760-3768.
Markus Priske, et al., "Reaction integrated separation of homogenous catalysts in the hydroformylation of higher olefins by means of organophilic nanofiltration" Journal of Membrane Science, vol. 360, XP027118372, 2010, pp. 77-83.

* cited by examiner

OPTIMIZED SEPARATION TECHNIQUE FOR WORK-UP OF HOMOGENEOUSLY CATALYSED HYDROFORMYLATION MIXTURES

The invention relates to a process for producing alcohols by homogeneously catalysed hydroformylation of olefins to aldehydes and subsequent hydrogenation thereof. The invention further relates to a plant for conducting the process. The main focus of the invention is on the separation technique for working up the hydroformylation mixture.

The hydroformylation reaction, which is also known as the oxo reaction, makes it possible to convert olefins (alkenes) with syngas (a mixture of carbon monoxide and hydrogen) into aldehydes. The aldehydes obtained then correspondingly have one carbon atom more than the olefins used. The subsequent hydrogenation converts the aldehydes into alcohols which, owing to their genesis, are also called "oxo alcohols".

Any olefin is hydroformylatable in principle, but the olefins used as a substrate in commercial hydroformylation usually have from two to 20 carbon atoms. Since the alcohols obtainable by hydroformylation and hydrogenation have a very wide variety of possible uses—as plasticizer for PVC, as detersives in laundry detergents and as scents for example—hydroformylation is practiced on a large industrial scale.

Isononanol, or INA for short, is one example of an oxo alcohol for which there is a high global demand. Isononanol is a mixture of isomeric nonyl alcohols such as, for example, n-nonanol and singly and/or multiply branched nonanols such as methyloctanol in particular. INA has the CAS number 27458-94-2 and is used mainly in plasticizer manufacture. To obtain the $C_9$ oxo alcohol INA, $C_8$ olefins such as, for example, 1-octene are hydroformylated to the corresponding $C_9$ aldehydes and they are subsequently hydrogenated.

Industrial methods of hydroformylation are classified in the main according to the substrate used, the catalyst system, the phase split in the reactor and the technique for discharging the reaction products from the reactor. The number of reaction steps involved is a further important technical aspect.

Either cobalt- or rhodium-based catalyst systems are used industrially, the latter being complexed with organophosphorus ligands such as phosphine, phosphite or phosphoramidite compounds. These catalyst systems are in the form of a homogeneous solution in the reaction mixture.

The hydroformylation reaction is usually carried out with two phases, a liquid phase which contains the olefins, the dissolved catalyst and the products, and a gas phase, which is formed essentially by syngas. The products of value are then removed from the reactor in liquid form (as a liquid recycle) or in gaseous form together with the syngas (in a gas recycle). The Ruhrchemie/Rhône-Poulenc process is a special case in that the catalyst is in an aqueous phase.

Some hydroformylation processes are also carried out in the presence of a solvent, for example alkanes in the feed mixture.

The present invention relates to homogeneously catalysed hydroformylation processes where the reactor effluent is liquid (i.e. a liquid recycle is operated).

Since the invention is essentially concerned with the technique of working up the reaction effluent, the voluminous prior art is referenced for the chemistry and reaction technology of hydroformylation. Worth reading are in particular:

Falbe, Jürgen: New Syntheses with Carbon Monoxide. Springer, 1980. (standard authority regarding hydroformylation)

Pruett, Roy L.: Hydroformylation. Advances in Organometallic Chemistry. Vol. 17 pages 1 to 60, 1979 (review paper)

Frohning, Carl D. and Kohlpaintner, Christian W.: Hydroformylation (Oxo Synthesis, Roelen Reaction). Applied homogeneous catalysis with organometallic compounds. Wiley, 1996. Pages 29 to 104. (review paper)

Van Leeuwen, Piet W. N. M and Claver, Carmen (Edit.): Rhodium Catalyzed Hydroformylation. Catalysis by Metal Complexes. Volume 22. Kluwer, 2000. (Monograph regarding Rh-catalysed hydroformylation. The emphasis is on the chemistry, but engineering aspects are also discussed.)

Detailed descriptions of processes for producing INA are found in the patent literature: DE102008007080A1 and EP2220017B1 disclose Co-based processes for production of INA. EP1674441B1 discloses a two-step INA process wherein a Co-catalysed hydroformylation is followed with an Rh-catalysed oxo reaction.

Notably the removal of Rh-based catalyst complexes from homogeneously catalysed hydroformylation mixtures proves to be a technical challenge. This is because, first, Rh is a very costly noble metal, losses of which must absolutely be avoided. Complete recovery of the rhodium from the product stream accordingly has to be an imperative. Since the Rh concentration in typical hydroformylation reactions is merely 20 to 100 ppm and a typical "world scale" oxo plant achieves an annual output of 200 000 tonnes, the separation equipment used not only has to be reliable in removing the low levels of Rh but also has to be able to cope with a high throughput. A complicating factor is that the organophosphorous ligands of the catalyst complex are very sensitive to changes of state and quick to deactivate. A deactivated catalyst can at best only be reactivated at considerable expense and inconvenience. Catalyst removal accordingly has to be done very gently. Energy efficiency is another important development objective for the separation unit operations.

Separation unit operation is used by a chemical engineer to refer to a measure where one composition of matter, containing two or more components, is converted into two or more compositions of matter having a different quantitative make-up than the starting composition. The compositions of matter obtained generally have a particularly high concentration of the desired component; ideally they are pure products. The objective of high purification/separation usually runs counter to the twin objectives of high throughput and low capital and energy requirements.

Separation processes can be classified according to the physical effect they rely on. Essentially three groups of separation processes are known for working up hydroformylation mixtures, namely thermal separation processes, adsorptive separation processes and membrane separation processes.

Thermal separation processes include distillations and rectifications. These separation processes, which are tried and tested on a large industrial scale, rely on the different boiling points of the components present in the mixture by vaporizing the mixture and selectively condensing the vaporizing components. High temperatures and low pressures in distillation columns lead to deactivation of the catalyst in particular. There have accordingly already been attempts to make the thermal work-up of hydroformylation mixtures particularly gentle:

EP1193239B1 describes an Rh-catalysed hydroformylation where product removal is via a thin film evaporator and/or a falling film evaporator. The catalyst is stabilized in the evaporator by maintaining a certain carbon monoxide partial vapour pressure. Thin film evaporators and falling film evaporators are special designs of apparatus for conducting thermal separation unit operations.

Thermal separation processes always have the disadvantage of high energy requirements. Membrane separation processes are distinctly more energy-efficient. The starting mixture is applied as a feed to a membrane having a differing permeability for the different components. Components for which the membrane has a particularly high permeability are collected on the other side of the membrane as the permeate and conducted away. Components which are preferentially held back by the membrane are collected on this side of the membrane as the retentate and conducted away. More than one separation effect is exploited in the membrane technology; solution and diffusion effects are relied on as well as size differences between the components (mechanical screening effect). The importance of solution and diffusion effects increases with the imperviousness of the separation-active layer of the membrane. An excellent introduction to membrane technology is offered by:

Melin/Rautenbach: *Membranverfahren. Grundlagen der Modul-und Anlagenauslegung*. Springer, Berlin Heidelberg 2004.

The possibilities of using membrane technology for working up hydroformylation mixtures are reported by Priske, M. et al.: Reaction integrated separation of homogeneous catalysts in the hydroformylation of higher olefins by means of organophilic nanofiltration. Journal of Membrane Science, Volume 360, Issues 1-2, 15 Sep. 2010, Pages 77-83; doi:10.1016/j.memsci.2010.05.002.

A large advantage of membrane separation processes versus thermal separation processes is the lower consumption of energy. However, catalyst complex deactivation is also a problem in membrane separation processes.

This problem was solved by the hydroformylation mixture work-up process described in EP1931472B1, wherein a certain carbon monoxide partial vapour pressure is maintained in the membrane feed, in the membrane permeate and in the membrane retentate. The result is the first effective use of membrane technology in industrial hydroformylation. In a particular embodiment, shown in FIG. 3 of EP1931472B1, two membrane separation units are combined with one thin film evaporator. The invention proceeds from this embodiment as closest prior art.

Membrane separation processes have a specific disadvantage in that this still comparatively young technology stands and falls with the availability of membranes. Specific membrane materials for the removal of catalyst complexes are still not available in large amounts. Yet the separation of large product streams requires very large membrane areas and hence a correspondingly large amount of membrane material and high capital costs.

Adsorptive separation processes are the third group of separation processes used in the clean-up of hydroformylation mixtures. They rely on the chemical or physical adsorption of substances out of fluids to another liquid or solid substance, the adsorbent. The adsorbent is introduced into a vessel and the mixture to be separated is flowed through it. The target substances carried by the fluid interact with the adsorbent and remain attached thereto such that the adsorber exit stream is depleted in (purified of) the adsorbed substances. Vessels filled with adsorbents are also known as scavengers in the art. There are reversible and irreversible adsorbers depending on whether the adsorber is able to release the adsorbed material again (i.e. to regenerate) or binds it irreleaseably. Since adsorbers are able to remove minuscule quantities of solid bodies from product streams, adsorptive methods of separation are particularly useful for final purification. They are unsuitable for initial purification, since the constant replacement of irreversible adsorbers and/or the constant regeneration of reversible adsorbers is industrially inconvenient and expensive.

Since adsorptive methods of separation are particularly useful for removing solids, they are virtually predestined for removing catalyst residues from reaction mixtures. Useful adsorbents include high-porosity materials such as, for example, activated carbon or functionalized silica.

WO2009049911A1 describes adsorbents for removing rhodium from reaction mixtures. The material is based on polysiloxanes modified with alkylurea- or alkylthiourea-type groups.

WO2006013060A1 discloses polysiloxanes modified with alkyl(thio)ether groups, which are likewise said to be useful as adsorbers for removing rhodium from reaction mixtures.

In WO2010097428A1, the removal of catalytically active rhodium complexes from hydroformylation reactions is accomplished by first passing the reaction mixture onto a membrane separation unit and then sending the Rh-depleted permeate into an adsorption step.

The technologies described in the patent literature discussed are all in principle useful for reprocessing hydroformylation mixtures. As usual, the particular separation techniques all have their specific advantages and disadvantages.

It is an object of the present invention to specify a process for reprocessing homogeneously catalysed hydroformylation mixtures which takes advantage of the specific advantages of the individual separation technologies while very largely avoiding the specific disadvantages. The most important objective here is to provide for catalyst removal which is very complete yet gentle and which is technically reliable and creates low capital and operating costs. The process shall be unreservedly suitable for processing the reaction effluent from "world scale" oxo plants.

We have found that this object is achieved by skillfully combining different separation technologies while complying with certain operating parameters. The required measures are recited in claim 1.

The invention accordingly provides a process for producing alcohols by homogeneously catalysed hydroformylation of olefins to aldehydes and subsequent hydrogenation thereof, comprising the steps of:

a) providing one or more olefins, syngas and a catalyst system and also optionally a solvent;

b) hydroformylating the olefin(s) in the presence of the syngas and of the catalyst system in one or more than one hydroformylation reactor to form at least aldehyde and also high boilers;

c) withdrawing a liquid hydroformylation effluent comprising aldehyde, olefin, dissolved syngas, catalyst system and high boilers from the hydroformylation reactor;

d) optionally devolatilizing the liquid hydroformylation effluent;

e) separating the liquid hydroformylation effluent in a first membrane separation unit into a product stream and a reactor return stream, wherein the catalyst system partitions into the reactor return stream;

f) returning the reactor return stream into the hydroformylation reactor;

g) optionally devolatilizing the product stream;

h) separating the product stream in a thermal separation unit into a gaseous head product comprising aldehyde and olefin and a liquid bottom product comprising aldehyde, high boilers and catalyst complex;

i) separating the bottom product in a second membrane separation unit into a permeate and a retentate, wherein the catalyst system partitions into the retentate;

k) wherein the thermal separation unit is operated such that 80% to 98% of the mass introduced into the thermal separation unit with the product stream re-emerges from the thermal separation unit as head product;

l) and wherein at least some of the head product of the thermal separation unit and the permeate of the second membrane separation unit is subjected to conjoint or separate hydrogenation.

A fundamental concept of the present invention is to run the thermal separation unit downstream of the first membrane separation unit under comparatively mild conditions in that 80 to 98% of the mass introduced into the thermal separation unit re-emerges therefrom as head product. Preferably, about 90% of the introduced mass is withdrawn as head product. The separation performance of this step or stage, then, falls far short of its technical capabilities, but has distinctly lower energy requirements. Compared with the conventional operation of a thermal separation unit, the mild operating conditions chosen for the purposes of the present invention have the consequence that the target product (the aldehyde) is not completely removed overhead, but that residual aldehyde remains in the pot in significant amounts. But the mild conditions in the thermal separation unit cause reduced deactivation of catalyst complex not retained in the first membrane separation unit.

This is because the first membrane separation unit is likewise not trimmed to complete removal of the catalyst complex, entailing a reduction in membrane area. Catalyst complex retention in the first membrane separation unit is preferably in the range from 60 to 90%, more preferably in the range from 70 to 80% and even more preferably equal to 75%.

The retention R of a membrane is determined via the local concentrations of a component i in the retained stream (retentate) and in the stream which permeates through the membrane (the permeate). When retentate and permeate are ideally mixed along the membrane, the local retentate and permeate concentrations correspond to the respective concentrations in the total retentate or, respectively, permeate obtained. The retention R of a membrane in respect of a component i in a feed stream is defined as follows:

$$R = 1 - c_{Pi}/c_{Ri}$$

where $c_{Pi}$ is the concentration of component i in permeate P and $c_{Ri}$ is the concentration of component i in retentate R. In the limiting case of complete retention of component i by the membrane, $c_{Pi}$ is =0 and R is =1. In the event of a preferential permeation of component i, $c_{Pi}$ is $>c_{Ri}$ and R is <0.

The catalyst which permeates through the first membrane separation unit and hence is not recycled ends up in the bottom product of the thermal separation unit and is only nearly fully removed in the second membrane separation unit and recycled as the retentate thereof. Since the bottom product stream of the thermal separation unit comprises between 2 and 20%, preferably about 10% of the entire mass introduced into the thermal separation unit, the second membrane separation unit has to cope with a distinctly lower mass flow than the first membrane separation unit and can accordingly accomplish nearly complete catalyst removal at an acceptable level of equipment requirements. More particularly, the low mass flow facilitates the economic use of a two-stage membrane separation unit, which provides better separation results. More on this later.

A further advantage of the described method of operating the thermal separation unit is that the high boilers which are formed in the hydroformylation reactor likewise become concentrated in the bottom product of the thermal separation unit and serve as solvent for the catalyst. Thus, the catalyst is removed from the effluent of the hydroformylation reactor in the first membrane separation unit, but from the high-boiler stream in the second membrane separation unit. Since the two membranes operate in different chemistries, the achievable overall removal performance can be micro-optimized. Micro-optimization is effected by suitably choosing the membrane material, the interconnection within the membrane separation stage and the operating conditions for the individual membranes.

Catalyst removal is also facilitated by the availability of membrane materials which are particularly suitable for use in high-boiler streams. At the same time, a return of high boilers into the hydroformylation reactor via the secondary circuit starting with the retentate of the second membrane separation unit is avoided, which prevents a build-up of high boilers in the reactor, which would impair the space-time yield of the reaction.

The accumulation of high boilers in the hydroformylation reactor can also be avoided when the retentate of the second membrane separation unit is not returned into the hydroformylation reactor, but is mixed with the liquid hydroformylation effluent withdrawn from the hydroformylation reactor and fed to the first membrane separation unit. The loop of the secondary circuit thus closes downstream and not upstream of the hydroformylation reactor.

This has the initial advantage that even when the membrane used is less selective with regard to high boilers, the high boilers are not fed into the hydroformylation as inert components. A high proportion of inert components in the reactor leads to yield losses. A further important advantage of returning the retentate of the second membrane separation unit into the feed to the first membrane separation unit instead of into the reactor feed is that it is easier to isolate the control technology for the membrane separation units from the control technology for the reactor to thereby reduce mutual interference. A hydroformylation reactor, especially when used to process raw materials of varying chemical composition, is in a less steady state than a separation apparatus. As a result, the control system for the reactor is distinctly more dynamic than that for the separation apparatuses. Recycling the retentate of the second membrane separation unit upstream of the reactor leads to further coupling of these control circuits, so any non-steady behaviour on the part of the reactor will also feed through to the membrane separation units. This problem is very largely avoided by recycling the retentate of the second membrane stage to a point downstream of the hydroformylation reactor. It will be appreciated that this advantage is also made use of when the membrane used in the second membrane separation unit has a high permeability to high boilers and so is used to remove high boilers from the system.

The proportion of catalyst which is not retained in the first membrane separation unit and hence is not recycled in the primary catalyst loop to a point upstream of the reactor is introduced into the thermal separation unit of the plant according to the present invention. At 75% retention in the first membrane separation unit, therefore, the remaining 25% of the catalyst-ligand complex pass into the thermal separation unit. The catalyst-ligand complex departs the thermal separation unit essentially via the bottom product stream thereof. However, it is likely that small amounts of catalyst become entrained in the vapour generated in the thermal separation unit and are carried off overhead. Hence the head product of the thermal separation unit will contain small amounts of catalyst.

To prevent these residual amounts from being carried off out of the plant together with the prevailing aldehyde in the head product and hence from being irretrievably lost, the head product of the thermal separation unit passes through an adsorber before hydrogenation in a preferred development of the invention. The adsorber catches the residual catalyst quantities and holds them back. Since the bulk of the catalyst residues are recycled via the first membrane separation unit and/or the bottom product of the thermal separation unit, only small amounts of catalyst are likely to be left in the head product of the thermal separation unit. Using the adsorber at this point is accordingly sensible.

The adsorber comprises a vessel which is packed with an adsorbent, such as a modified silica or activated carbon for example, and through which the condensed head product flows. The adsorber has no moving parts nor any energy requirements of its own, so its operating costs are comparatively low. Since only small amounts of catalyst to be adsorbed are likely and the catalyst is distinctly dearer than the adsorbent, it is economical to use an irreversible adsorbent.

Putting the adsorber upstream of the hydrogenation has the advantage that there is no rhodium to come down within the hydrogenation reactor. This is because, although an industrial hydrogenation reactor does have the ability to adsorb rhodium, the metals separate out onto the inner wall of the reactor, whence they can only be removed again with great difficulty. Recovering the rhodium from the adsorbent is much simpler. It is accordingly sensible to adsorb the catalyst upstream of the hydrogenation. Moreover, a dedicated adsorber provides a sharper separation and hence is more selective than a hydrogenation reactor.

It can further not be ruled out that very small quantities of catalyst do slip through the second membrane separation unit. Although the second membrane separation unit is designed to achieve nearly complete recycling of the catalyst via the secondary circuit, not even a membrane ever achieves ideal separation. The catalyst which slips through the second membrane separation unit to end up in its permeate should accordingly be protected from loss in a preferred development of the invention wherein the permeate of the second membrane separation unit passes through an adsorber before hydrogenation. With regard to the adsorber downstream of the second membrane separation unit, the observations made regarding the adsorber downstream of the thermal separation unit apply in principle.

The adsorptively purified streams—head product of the thermal separation unit and the permeate of the second membrane separation unit—are separately or conjointly subjected to a hydrogenation. The hydrogenation has the primary purpose to convert the aldehydes formed in the hydroformylation into the corresponding alcohols. Yet a hydrogenation of the aldehydes already takes place in the oxo reactor as a consecutive reaction to the hydroformylation; but in the case of Rh-catalysed oxo processes this only amounts to about 3%. Hydrogenation in the hydroformylation reactor is at best tolerated as a consecutive reaction which does not bring about the required yield of alcohols. The hydrogenation reactor does the main share of hydrogenation. Besides, the reaction conditions in the hydrogenation reactor are most suitable for this reaction and appropriate catalysts are present. A further function of hydrogenation is to convert residual olefins, unconverted in the oxo reaction, into alkanes and thereby reduce their reactivity. Some of the olefins are incidentally also hydrogenated in the oxo reactor.

The alcohols produced according to the present invention are thus at the latest obtained downstream of the hydrogenation. They form part of the hydrogenation mixture withdrawn from the hydrogenation reactor and are accompanied by said alkanes as low boilers as well as by hydrogenated high boilers. In a preferred development of the invention, the hydrogenation mixture withdrawn from the hydrogenation is subjected to a thermal work-up to obtain an alcohol-rich fraction, a low-boiler fraction and a high-boiler fraction.

The hydrogenation mixture is worked up using conventional distillation technology, since it is tried and tested and, what is more, catalyst residues are no longer a factor which has to be taken into account. The work-up is thermal and is preferably effected in three steps using three serially connected distillation columns:

A first distillation column, where the low-boiler fraction is removed from the hydrogenation mixture overhead. The high boilers and also the alcohol collect at the base of the first distillation column. The low-boiler fraction removed overhead is removed from the system and marketed as a product of value. When, for example, C9 alcohols are produced from C8 olefins, the low-boiler fraction comprises predominantly C8 alkanes and also a small amount of C9 aldehyde left unconverted in the hydrogenation. Such a "light oxo fraction" can be used as a solvent in various sectors.

A second distillation column, which is then fed with the mixture of high boilers and alcohols which leaves the first distillation column as the bottom product thereof. An alcohol-rich fraction is removed in the second distillation column overhead as the actual main product of value of the process according to the present invention. The bottom product of the second distillation column is predominantly made up of the high-boiler fraction accompanied by residual alcohol.

A third distillation column, which is fed with the bottom product of the second distillation column and which removes the remaining alcohol overhead. The high-boiler fraction is obtained in the bottom product of the third distillation column and is marketed as a by-product. The "heavy oxo fraction" obtained in this way comprises a high-boiling liquid having a high flash point, which is predominantly used as a solvent in the mineral oil industry, as an auxiliary in the paint, leather and rubber industries and also in paper and textile manufacture.

Depending on the operation mode of the oxo reaction, the conversion of the introduced alkenes is not complete. In practice, the conversion may be limited to about 93%, meaning that about 7% of the introduced alkenes re-emerge from the oxo reactor together with the reaction mixture. The unconverted alkenes are lost in the hydrogenation at the latest. To prevent this, the hydrogenation may also be placed downstream of the product separation stage, and therefore the low boilers fraction also contains the unconverted alkenes. These can then be returned into the oxo reactor for renewed subjection therein to hydroformylation. In this way, the loss of alkenes is reduced. If, therefore, the hydrogenation is placed downstream of the product separation stage, the head product of the thermal separation unit is fed to the hydrogenation in part only, not as a whole; the alkenes present therein are recycled into the oxo reaction. The disadvantage of this embodiment is that a separate hydrogenation has to be provided for each of the fractions obtained.

Following this digression into the work-up of the hydrogenation mixture and the placement of the hydrogenation, back to the chiefly interesting work-up of the hydroformylation effluent:

The thermal separation unit is most simply realised as a distillation column. In a preferred embodiment of the invention, however, the thermal separation unit comprises a thin film evaporator and a falling film evaporator, wherein the thin film evaporator and the falling film evaporator are serially interconnected. The thin film evaporator is in this case preferably arranged downstream of the falling film evaporator. Thin film evaporators and falling film evaporators are thermal separation apparatuses known per se.

A thin film evaporator has an essentially cylindrical steam-heated inner wall whereto a thin film of the starting mixture is applied by rotating distributor elements. The mechanically driven distributor elements ("wipers") are needed to apply and distribute the mixture which rapidly evaporates on the plates.

A falling film evaporator comprises an essentially vertical, externally heated tube whose inside surface is covered with a descending and evaporating thin film of the starting mixture. The unevaporated components are withdrawn as bottom product at the basal end of the tube, while the evaporated components depart at the other end of the tube as head product. There are accordingly no moving parts in a falling film evaporator.

What thin film evaporators and falling film evaporators have in common as a design feature is thus at least one heated evaporation element whereto a thin film of the liquid starting mixture is applied and on which it is partly evaporated. A detailed description of thin film evaporators and falling film evaporators is found in ULLMANN:

Billet, Reinhard: Evaporation. Ullmann's Encyclopedia of Industrial Chemistry. Published Online: 15 Jun. 2000 DOI: 10.1002/14356007.b03_03

It is alternatively possible to realise the thermal separation unit using two or three serially connected falling film evaporators. This facilitates area and residence-time minimization, increases the operational flexibility and leads to a separation which is particularly benign for the catalyst.

The separation apparatuses for realising the thermal separation unit are preferably operated at a negative pressure between 3 and 500 hPa.

The first membrane separation unit is most simply embodied as a feed-and-bleed system having a single recirculation loop. In the recirculation loop, some of the retentate is recycled into the feed.

Permeate quality can be improved for a start by constructing the membrane separation unit to have two or more serial loops.

Permeate quality can further be improved by using a multistage feed-and-bleed system as membrane separation unit. This is in effect a multistage membrane cascade having two or more recirculation loops. Cascaded feed-and-bleed membrane systems can be constructed either as a "depleting cascade" or as an "enricher cascade". Every stage of such a cascade can be constructed with one or more loops.

Compared with a "Christmas tree" formation likewise customary in membrane technology, feed-and-bleed membrane cascades can be operated under qualitatively and/or quantitatively fluctuating feed conditions and/or as membrane performance changes over time. When concentration factors are high, a depleting cascade leads to better overall permeate quality than an enriching cascade for the same installed membrane area. An enriching cascade further has the disadvantage that the area needed is more than twice as large compared with a single-stage membrane separation unit. In a depleting cascade, by contrast, virtually any desired membrane area between a single-stage membrane separation unit and an enriching cascade can be used. This is particularly important when an enriching cascade is not economical on account of the large membrane area needed and a single-stage membrane separation unit is unusable on account of insufficient separation performance.

These reasons suggest using a two-stage membrane cascade with partial recycling of permeate as first membrane separation unit. The permeate therein is recycled from the recirculation loop or the loops with the poorest permeate quality, which are generally the loops having the highest retentate concentration at the end of the concentrating sector. This array is known as "two-stage depleting cascade" in membrane technology. The recirculation loops with permeate recycling at the end of the cascade are also referred to as concentrate loops. Combining concentrate loops with permeate recycling facilitates purer overall permeate.

It is very particularly preferable for the membrane area used for the concentrate loops to be made smaller than the membrane area used for the other loops. This reduces membrane area requirements without sacrificing the separation result.

The second membrane separation unit is preferably configured as a two-stage enriching cascade. At a two-stage enriching cascade is a multistage membrane cascade with partial recycling of retentate. Total retentate from the second stage is recycled therein. Both the first and the second stage of the two-stage enriching cascade can be constructed with one or more membrane loops. First, the concentrating factors needed here are low enough for an enriching cascade to be advantageous over a depleting cascade on account of the separation result. Secondly, the permeate quantities to be generated and hence the membrane areas needed are so small that an enriching cascade is economical.

The method which the present invention provides for working up hydroformylation mixtures can in principle be applied to any homogeneous catalysed hydroformylation with liquid recycle. However, it is preferably applied to rhodium-catalysed hydroformylations, since these catalyst systems require particularly careful catalyst removal on account of the high rhodium price. The invention is most preferably applied to processes wherein a rhodium system having an organophosphorus ligand is used as catalyst. Organophosphorus ligands include phosphines, phosphites and phosphoramidites. It is particularly interesting to use rhodium catalysts with phosphite ligands, since they are notable for their particularly high selectivity. Phosphites, however, have a particular propensity for decomposition. Since the process of the present invention is directed to particularly benign catalyst removal, it facilitates the economic use of rhodium-phosphite systems on an industrial scale.

Since the chemistry and reaction technology of rhodium-catalysed hydroformylation is described at length in Van Leeuwen, Piet W. N. M and Claver, Carmen (Edit.): Rhodium Catalyzed Hydroformylation. Catalysis by Metal Complexes. Volume 22. Kluwer, 2000, no further observations are needed.

The process of the present invention can in principle utilize any hydroformylatable olefin. Olefins having 2 to 20 carbon atoms are generally hydroformylatable. Depending on the catalyst system used, both terminal and non-terminal olefins can be hydroformylated.

Rhodium-phosphite systems can utilize not only terminal but also non-terminal olefins as a substrate.

The olefins used need not be used as a pure material; on the contrary, olefin mixtures can also be used as reactant. Olefin mixtures, on the one hand, are mixtures of various isomers of olefins having a single number of carbon atoms; on the other, however, an olefin mixture may also comprise olefins having different numbers of carbon atoms and isomers thereof. It is very particularly preferable to use olefins having 8 carbon atoms in the process, to accordingly hydroformylate them to aldehydes having 9 carbon atoms and then for the aldehydes to be hydrogenated into alcohol having 9 carbon atoms. Isononanol (INA) is obtained from the $C_8$ olefins in this way.

The process of the present invention is implemented and embodied in a corresponding plant for the production of alcohol. A plant of this type likewise forms part of the subject matter of the present invention. The plant of the present invention includes the following apparatuses:
 a) one or more than one hydroformylation reactor having a reactant inlet and a product outlet,
 b) a first membrane separation unit having a first membrane entry point, a first permeate connection point and a first retentate connection point,
 c) a thermal separation unit having a product inlet, a head product connection point and a bottom product connection point,
 d) a second membrane separation unit having a second membrane entry point, a second permeate connection point and a second retentate connection point,
 e) one or more than one hydrogenation reactor having an aldehyde entry point and an alcohol exit point.

These apparatuses connect to each other in material communication as follows:
 f) the product outlet of the hydroformylation reactor connects directly or via a devolatilizer to the first membrane entry point of the first membrane separation unit,
 g) the first retentate connection point of the first membrane separation unit connects to the reactant inlet of the hydroformylation reactor,
 h) the first permeate connection point of the first membrane separation unit connects directly or via a devolatilizer to the product inlet of the thermal separation unit,
 i) the bottom product connection point of the thermal separation unit connects to the second membrane entry point of the second membrane separation unit,
 k) the head product connection point of the thermal separation unit connects directly or via an adsorber to the aldehyde entry point of the hydrogenation reactor,
 l) the second retentate connection point of the second membrane separation unit connects together with the product outlet of the hydroformylation reactor to the first entry point of the first membrane separation unit,
 m) the second permeate connection point of the second membrane separation unit connects directly or via the adsorber to the aldehyde entry point of the hydrogenation reactor.

The special feature of the plant is that the secondary catalyst recycle proceeding from the second retentate at the end of the second membrane separation unit connects to the entry point of the first membrane separation unit and not to the entry point of the hydroformylation reactor. This prevents high-boiler formation in the hydroformylation reactor and improves particularly the controllability of the plant according to the present invention.

A further special interconnection feature of this plant is that the two decatalysed product streams from the top of the thermal separation unit and from the permeate of the second membrane separation unit connect to the aldehyde entry point of the hydrogenation reactor.

The invention further provides for the use of this plant for conducting a process according to the present invention.

Further preferred embodiments of the invention will become apparent from the following detailed description of a plant according to the present invention and of the process according to the present invention which is carried out using a plant according to the present invention:

FIG. 1 shows a flow diagram of a first embodiment comprising two separate adsorbers, FIG. 2 shows a flow diagram of a second embodiment of an inventive plant comprising a conjoint adsorber, FIG. 3 shows a detailed depiction of the purifying stage, FIG. 4 shows a first embodiment of the thermal separation unit, consisting of a falling film evaporator and a thin film evaporator, FIG. 5 shows a second embodiment of the thermal separation unit, consisting of two falling film evaporators, FIG. 6 shows a detailed depiction of a first membrane separation unit as a two-stage depleting cascade, and FIG. 7 shows a detailed depiction of a second membrane separation unit as a two-stage enriching cascade.

Figure 1:
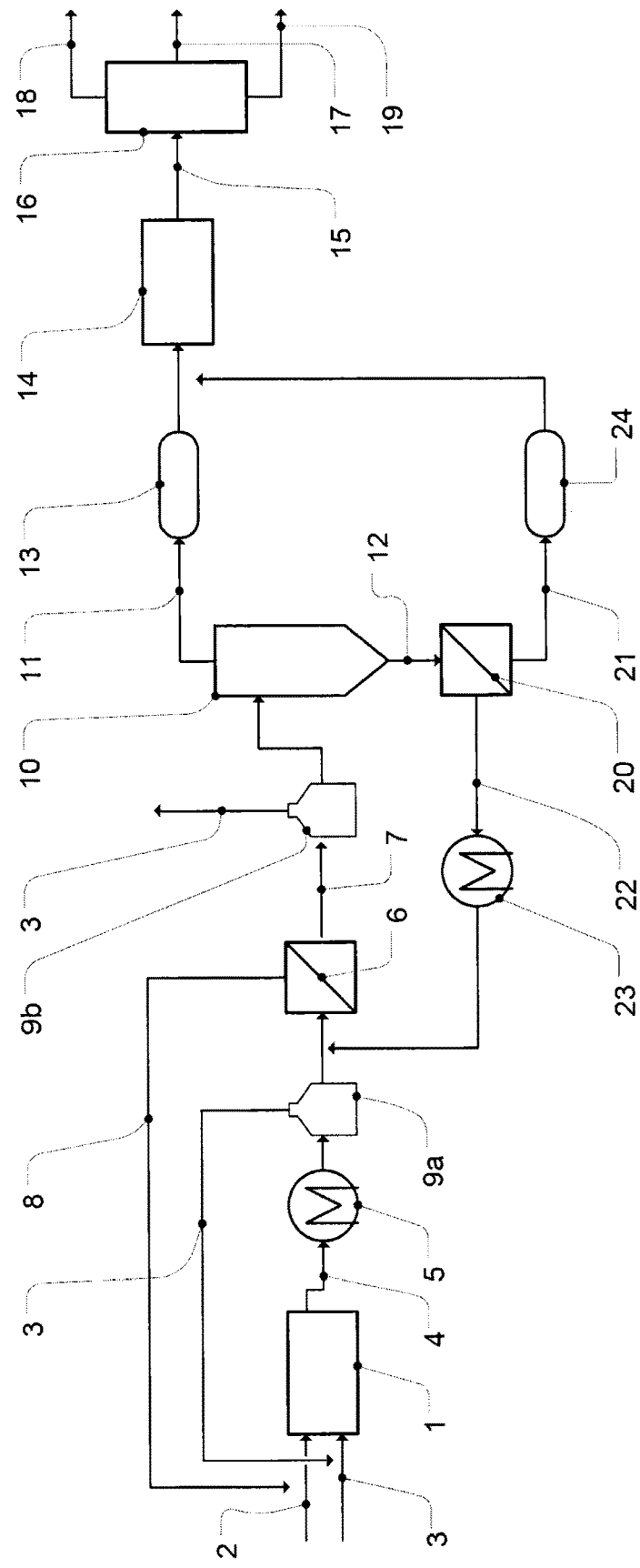

FIG. 1 shows the flow diagram of an inventive plant with which the inventive process can be carried out. The flow diagram is simplified for clarity, as usual. Self-evident plant components such as valves, pumps and the like are not depicted.

At the heart of the plant is a hydroformylation reactor 1. This is where the hydroformylation reaction takes place. An olefin 2 is reacted with syngas 3—a mixture of carbon monoxide and hydrogen—in the presence of a homogeneously dissolved catalyst to corresponding aldehydes having one carbon atom more. This reaction is a gas/liquid phase reaction wherein the olefin and the reaction products are in the liquid phase, while one portion of syngas 3 forms the gaseous phase and another portion of the syngas is dissolved in the liquid phase. A homogeneous catalyst complex is likewise dissolved in the liquid phase.

Optionally, a solvent can be supplied to the hydroformylation reactor 1, for example alkanes to accompany the olefin used. The hydroformylation then takes place in the presence of the optional solvent.

Any type of reactor design which permits a gas-liquid phase reaction is possible in principle. A bubble column reactor is used with preference. Bubble column reactors are general common knowledge in the prior art and are described at length in ULLMANN:

Deen, N. G., Mudde, R. F., Kuipers, J. A. M., Zehner, P. and Kraume, M.: Bubble Columns. Ullmann's Encyclopedia of Industrial Chemistry. Published Online: 15 Jan. 2010. DOI: 10.1002/14356007.b04_275.pub2

Since bubble column reactors are not infinitely scalable owing to their flow behaviour, two or more comparatively small reactors connected in parallel have to be provided instead of a single large reactor for a plant designed to have a very large manufacturing capacity. A world-scale plant with a rating of 30 t/h may have two or three bubble columns each of 15 t/h or, respectively, 10 t/h capacity. The reactors operate in parallel under the same reaction conditions. Connecting two or more reactors in parallel also has the advantage that the reactor does not have to be run in the energetically unfavourable partial-load range when plant utilization is lower. Instead, one of the reactors is switched off completely and the other reactor continues to be run under full load. A triple arrangement can accordingly respond even more flexibly to demand changes.

Any reference herein to a hydroformylation reactor is thus not necessarily to be understood as meaning one apparatus. Two or more mutually interconnected reactors may also be intended.

The reaction is carried out under customary conditions. A temperature of 120° C. to 160° C. and a pressure of 20 to 28 MPa are particularly preferred. A conversion of >90% is sought under these conditions. Syngas having a hydrogen/carbon monoxide ratio of 1:1 is fed into the reactor in excess.

Any olefin amenable to the oxo reaction is useful in principle as substrate for the hydroformylation. These are the olefins having two to twenty carbon atoms in particular. C6-C12 Olefin mixtures are used with particular preference. INA production utilizes olefin mixtures having a high isooctene content, for example the di-n-butene (CAS number 10071-47-9) available from Evonik Industries.

The following homogeneous catalysts are useful as catalyst system:

Rhodium-phosphite systems are used as homogeneous catalyst in particular. Rhodium nonanoate and tris(2,4-di-tert-butylphenyl)phosphite is an example of such a system. Metal concentration should be between 5 and 100 ppm and the ligand/rhodium ratio should preferably be about 5:1.

The hydroformylation produces not only the desired aldehydes but also in a consecutive secondary reaction, the corresponding alcohols and also high boilers. The high boilers include inter alia dimers, trimers, aldol products, Tishchenko products, esters and ethers. High-boiler formation in the reaction is unwanted, since it leads to yield losses, but is technically impossible to fully avoid. High boilers therefore have to be removed from the system at a rate commensurate with their rate of formation. High boilers are so called because these substances have a higher boiling point than the aldehyde, and so high boilers collect at the base of the thermal separation unit and/or of the distillation downstream of the hydrogenation. By contrast, low boilers include olefins, alkanes and aldehydes formed in the hydroformylation or hydrogenation or already present in the olefin mixture.

Reactor 1 has withdrawn from it a liquid hydroformylation effluent 4 which as well as the desired aldehyde also contains unconverted olefin, syngas dissolved in the liquid, the homogeneously dissolved catalyst system, further low boilers and the high boilers. Any optional solvent used forms part of the low boilers.

The hydroformylation effluent 4 is cooled down to a temperature of about 40 to 50° C. in a first heat exchanger 5. The hydroformylation effluent 4 is decompressed to about 0.5 MPa in a first devolatilizer 9a, the effervescing syngas 3 being returned into reactor 1. The hydroformylation effluent 4 is then applied to a first membrane separation unit 6. The membrane separation unit 6 comprises a multistage depleting cascade, which is more particularly elucidated with reference to FIG. 6. For the purposes of understanding the functional interrelationships, however, it is sufficient to view the first membrane separation unit 6 as a single membrane.

The incoming hydroformylation effluent 4 in the first membrane separation unit 6 is separated therein into a product stream 7 and a reactor return stream 8, while the catalyst system in hydroformylation effluent 4 partitions into the reactor return stream 8. The product stream 7 is the permeate of the first membrane separation unit 6, while the reactor return stream 8 forms the retentate of the first membrane separation unit 6. Since the first membrane separation unit 6 allows the catalyst system to pass at a distinctly lower rate than the other constituents of the hydroformylation effluent 4, the catalyst system collects in the reactor return stream 8. The membrane separation unit 6 is preferably operated such that about three-quarters of the catalyst system removed from the hydroformylation reactor 1 ends up in the reactor return stream 8. The first membrane separation unit thus has a 75% retention with regard to the catalyst system. The following operating parameters must be observed for this:

Membrane temperature is between 20 and 160° C., preferably between 25 and 90° C. and more preferably between 30 and 60° C. A 10 to 30 K higher temperature can be advantageous in the concentrate loops. Transmembrane pressure difference is between 1 and 10 MPa, preferably between 1.5 and 5 MPa. It is particularly preferable to operate the membrane at about 2.5 to 3.5 MPa transmembrane pressure. The spiral-wound element is the membrane module design which is used with preference.

Preference is given to using membranes having a separation-active layer composed of a material selected from cellulose acetate, cellulose triacetate, cellulose nitrate, regenerated cellulose, polyimides, polyamides, polyetheretherketones, sulphonated polyetheretherketones, aromatic polyamides, polyamideimides, polybenzimidazoles, polybenzimidazolones, polyacrylonitrile, polyaryl ether sulphones, polyesters, polycarbonates, polytetrafluoroethylene, polyvinylidene fluoride, polypropylene, terminally or laterally organomodified siloxane, polydimethylsiloxane, silicones, polyphosphazenes, polyphenyl sulphides, polybenzimidazoles, 6.6 Nylon®, polysulphones, polyanilines, polypropylenes, polyurethanes, acrylonitrile/glycidyl methacrylate (PANGMA), polytrimethylsilylpropynes, polymethylpentynes, polyvinyltrimethylsilane, polyphenylene oxide, alpha-aluminas, gamma-aluminas, titanias, silicas, zirconias, silane-hydrophobicized ceramic membranes as described in EP 1 603 663 B1, polymers with intrinsic microporosity (PIM) such as PIM-1 and others, as described for example in EP 0 781 166 and in "Membranes" by I. Cabasso, Encyclopedia of Polymer Science and Technology, John Wiley and Sons, New York, 1987. The abovementioned chemistries can be in crosslinked form, optionally as a result of the addition of co-chemistries, in the separation-active layer in particular, or, as mixed matrix membranes, be provided with fillers such as, for example, carbon nanotubes, metal organic frameworks or hollow spheres and also particles of inorganic oxides or inorganic fibres, for example ceramic or glass fibres.

Particular preference is given to using membranes where the separation-active layer is a polymer layer composed of terminally or laterally organomodified siloxane, polydimethylsiloxane or polyimide which are constructed from polymers with intrinsic microporosity (PIM) such as PIM-1, or wherein the separation-active layer is built over a hydrophobicized ceramic membrane.

Very particular preference is given to using membranes composed of terminally or laterally organomodified siloxanes or polydimethylsiloxanes. Membranes of this type are commercially available.

In addition to the abovementioned materials, the membranes may comprise further materials. More particularly, the membranes may comprise scaffolding or support materials whereto the separation-active layer is applied. In composite membranes of this type, a scaffolding material is present alongside the actual membranes. A selection of scaffolding materials are described in EP 0 781 166, hereby incorporated herein by reference.

A selection of commercially available solvent-stable membranes are the MPF and Selro series from Koch Membrane Systems, Inc., different types of Solsep BV, the Starmem™ series from Grace/UOP, the DuraMem™ and PuraMem™ series from Evonik Industries AG, the NanoPro series from AMS Technologies, the HITK-T1 from IKTS, and also oNF-1, oNF-2 and NC-1 from GMT Membrantechnik GmbH and the Inopor®nano types from Inopor GmbH.

The retentate of the first membrane separation unit 6—referred to herein as reactor return stream 8 or else as primary recyclate—contains not only the high rhodium concentration but also the other chemistries of the hydroformylation effluent, namely aldehyde, olefin, dissolved syngas, further low boilers and high boilers. The reactor return stream 8 is returned into the hydroformylation reactor 1. The reactor return stream—contrary to the simplifying drawing—need not be fed into reactor 1 together with fresh olefin 2 and fresh syngas 3. It is perfectly conceivable for these three streams to be fed separately into the hydroformylation reactor 1 at different places.

In order that the catalyst system may not lose its activity in the first membrane separation unit 6, this membrane separation step is conducted by maintaining a minimum CO partial vapour pressure. It should be, as described in EP1931472B1, at least 100 kPa. Therefore, decompression in devolatilizer 9a is not complete, but only down to 0.5 MPa. This is because the dissolved syngas is only supposed to be removed downstream of the membrane. For this, product stream 7 is decompressed in a second devolatilizer 9b to atmospheric pressure. The syngas remaining in the permeate of the first membrane separation unit escapes completely in the process and is removed from the plant.

The devolatilized product stream 7 is then transferred into a thermal separation unit 10. This is most simply a distillation column, but preferably is a combination of a thin film evaporator and a falling film evaporator (cf. FIG. 4) or a combination of two or three falling film evaporators (cf. FIG. 5).

Product stream 7 is evaporated in the thermal separation unit 10 by the action of heat. For this, the temperature at the base of the falling film evaporator is set to 90° C.; the temperature at the base of the thin film evaporator is 100° C. Evaporation is supported by an applied vacuum of about 30 hPa in both cases. In this way, more than 90% of the mass introduced into the thermal separation unit 10 with product stream 7 is evaporated. This vaporous mass forms the head product 11 of the thermal separation unit. Since the introduced components have different boiling points it is not just a purely quantitative separation of product stream 7 which is brought about by the evaporation but also a qualitative one: Aldehyde, alcohol and the other low boilers preferentially partition into head product 11 because of their lower boiling points. The unevaporated components form a liquid bottom product 12 consisting essentially of high boilers, aldehyde and catalyst system, wherein aldehyde and high boilers account for approximately the same weight fraction. The operating conditions of the thermal separation unit are so chosen that preferably 95% of the aldehydes introduced with product stream 7 end up in head product 11. Not more than 5% of the aldehydes introduced with product stream 7 remain in bottom product 12.

The large stream withdrawn as top product 11, which contains the products of value, is then run through a first adsorber 13. Adsorber 13 has the function to catch residual quantities of catalyst, especially noble metal, entrained in droplets with the vapour. This is accomplished by using a conventional adsorbent such as activated carbon, silicates or aluminas, which are used in the form of a fixed bed. The adsorption is conducted at a temperature between 30 and 140° C. and space velocities of 0.01 to 5 1/h.

Head product 11, now completely purified of its catalyst load, is then subjected to a hydrogenation 14. The hydrogenation takes place in two serially connected hydrogenation reactors. The first reactor is operated in loop mode, the second in straight-path mode. Hydrogenation takes place in the liquid phase in a temperature range from 120 to 220° C., preferably at a temperature of 160° C. under adiabatic conditions. Pressure is from 1.5 to 30 MPa. Hydrogenation is effected in a heterogeneous fixed-bed catalyst such as, for example, copper, cobalt, copper-nickel, copper-chromium, copper-chromium-nickel, zinc-chromium or nickel-molybdenum catalysts, which may optionally include still further elements. Details for designing a suitable hydrogenation are described in EP0987240B1 and EP0987241B1, and also in DE102008007080A1.

Hydrogenation 14 exits into hydrogenation mixture 15 comprising essentially alcohol, alkanes (from unconverted olefins) and also hydrogenated low boilers and high boilers. Hydrogenation mixture 15 is then sent to a thermal work-up 16 and split therein into an alcohol-rich fraction 17, a low-boiler fraction 18 and a high-boiler fraction 19. The alcohol-rich fraction 17 is the actual product of value of the process according to the present invention. The low boilers 18 and high boilers 19 are by-products which can be marketed for subordinate purposes. The thermal work-up 16 of the three fractions 17, 18 and 19 from hydrogenation mixture 15 will be further elucidated with reference to FIG. 3.

In the event that the conversion of alkenes in the hydroformylation is incomplete, head product 11 of thermal separation unit 10 will contain a sizeable quantity of unconverted alkenes. In order that these may not be lost in hydrogenation 14, the hydrogenation may also be placed downstream of the thermal work-up, specifically one hydrogenation for the alcohol-rich fraction 17 (which in this case is more aldehyde-rich) and one hydrogenation for the high boilers fraction 19. The low boilers fraction 18 then contains the unconverted alkenes and can be returned into the hydroformylation reactor 1 (as is not shown in this figure). In the event of an alkene recycle, the head product 11 is thus fed into the hydrogenation in part only, not as a whole; the alkenes are first separated off and recycled.

As mentioned, bottom product 12 of thermal separation unit 10 contains essentially the high boilers, minor amounts of aldehyde and catalyst. The mass flow of bottom product 12 is distinctly less than that of the head product. When the product stream is 30 tonnes per hour and the proviso that 90% of introduced mass departs the thermal separation unit 10 overhead is observed, then the mass flow of bottom product 12 is merely 3 t per hour, i.e. ⅒ of that of the head product.

Bottom product 12 is then applied to a second membrane separation unit 20. Bottom product 12 is therein separated into a permeate 21 and a retentate 22, with the catalyst system partitioning into the retentate 22, since the second membrane separation unit 20 retains the catalyst system preferentially. Owing to the low mass stream with which the second membrane separation unit 20 has to cope compared with the first membrane separation unit 6, the catalyst in bottom product 12 can be nearly completely retained and collected in retentate 22. This is accomplished particularly when the choice of membrane material is particularly permeable for high boilers and hence passes the high boilers into permeate 21. Retentate 22 then consists essentially of aldehyde and catalyst.

The separation in the second membrane separation unit 20 is effected at a temperature between 20 and 160° C., preferably between 25 and 90° C. and more preferably between 30 and 60° C. The transmembrane pressure difference is between 1 to 10 MPa, preferably between 1.5 and 5 MPa. It is particularly preferable to operate the membrane at about 2.5 to 3.5 MPa transmembrane pressure. The spiral-wound element is the membrane module design which is used with preference.

The first and second membrane units can use the same or different membrane materials.

The classes of materials described hereinbelow are useful as membrane material for the second membrane separation unit 20:

Preference is given to using membranes within the second membrane separation unit having a separation-active layer composed of a material selected from cellulose acetate, cellulose triacetate, cellulose nitrate, regenerated cellulose, polyimides, polyamides, polyetheretherketones, sulphonated polyetheretherketones, aromatic polyamides, polyamideimides, polybenzimidazoles, polybenzimidazolones, polyacrylonitrile, polyaryl ether sulphones, polyesters, polycarbonates, polytetrafluoroethylene, polyvinylidene fluoride, polypropylene, terminally or laterally organomodified siloxane, polydimethylsiloxane, silicones, polyphosphazenes, polyphenyl sulphides, polybenzimidazoles, 6.6 Nylon, polysulphones, polyanilines, polypropylenes, polyurethanes, acrylonitrile/glycidyl methacrylate (PANGMA), polytrimethylsilylpropynes, polymethylpentynes, polyvinyltrimethylsilane, polyphenylene oxide, α-aluminas, γ-aluminas, titanias, silicas, zirconias, silane-hydrophobicized ceramic membranes as described in EP 1 603 663 B1, polymers with intrinsic microporosity (PIM) such as PIM-1 and others, as described for example in EP 0 781 166 and in "Membranes" by I. Cabasso, Encyclopedia of Polymer Science and Technology, John Wiley and Sons, New York, 1987. The abovementioned chemistries can be in crosslinked form, optionally as a result of the addition of cochemistries, in the separation-active layer in particular, or, as mixed matrix membranes, be provided with fillers such as, for example, carbon nanotubes, metal organic frameworks or hollow spheres and also particles of inorganic oxides or inorganic fibres, for example ceramic or glass fibres.

Particular preference is given to using membranes where the separation-active layer is a polymer layer composed of terminally or laterally organomodified siloxane, polydimethylsiloxane or polyimide which are constructed from polymers with intrinsic microporosity (PIM) such as PIM-1, or wherein the separation-active layer is built over a hydrophobicized ceramic membrane.

A detailed description of such membranes for use in high-boiler removal is found in EP2401078A1.

Very particular preference is given to using membranes composed of terminally or laterally organomodified siloxanes or polydimethylsiloxanes. Membranes of this type are commercially available.

In addition to the abovementioned materials, the membranes may comprise further materials. More particularly, the membranes may comprise scaffolding or support materials whereto the separation-active layer is applied. In composite membranes of this type, a scaffolding material is present alongside the actual membranes. A selection of scaffolding materials are described in EP0781166, hereby incorporated herein by reference.

A selection of commercially available solvent-stable membranes are the MPF and Selro series from Koch Membrane Systems, Inc., different types of Solsep BV, the Starmem™ series from Grace/UOP, the DuraMem™ and PuraMem™ series from Evonik Industries AG, the NanoPro series from AMS Technologies, the HITK-T1 from IKTS, and also oNF-1, oNF-2 and NC-1 from GMT Membrantechnik GmbH and the Inopor®nano types from Inopor GmbH.

The second membrane separation unit 20 is configured as a multistage enriching cascade. This membrane arrangement will be more particularly elucidated with reference to FIG. 7. To understand the function of second membrane separation unit 20 it is sufficient to assume that a single membrane is concerned.

The second membrane separation unit 20 has withdrawn from it the retentate 22 which is cooled down to about 40 to 50° C. in a heat exchanger 23 and then mixed with the likewise cooled-down hydroformylation effluent 4 and returned into the first membrane separation unit 6. Returning the secondary recyclate (retentate 22) into the first membrane separation unit 6 at a point upstream of hydroformylation reactor 1 offers the decisive advantage of reducing interference between the control of the second membrane separation unit 20 and that of hydroformylation reactor 1. It also stops aldehyde being unnecessarily passed back into the reaction together with retentate 22 and reducing the yield of said reaction. The catalyst constituents returned via the secondary return stream 22 are very largely rejected again by the first membrane separation unit 6 and fed back into reactor 1 via the primary reactor return stream 8.

The second membrane separation unit 20 provides the permeate 21, which very largely consists of high boilers and residual aldehyde and is passed through a second adsorber 24 to trap and secure residual quantities of catalyst. To remove noble catalyst metals from the liquid permeate 21, the adsorption is carried out at a temperature of 30 to 140° C. and space velocities of 0.01 to 5 1/h. The adsorbent is preferably used in the form of a fixed bed.

Useful adsorbents include particularly activated carbon, surface-rich polysilicic acids such as silica gels (silicic xerogels), finely divided silica, surface-rich aluminas and alumina hydrates as well as spent or virgin (hydrogenation) catalysts.

Chemically modified silica materials as disclosed in WO 2006013060 A1 have been found to be particularly advantageous adsorbents. Adsorbents of this type are available under the article name of Mercaptoalkyl-modified Silica, Type Rh H3, Batch No. 09-S26-001 from PhosphonicS Ltd, 114 Milton Park, Abingdon, OXON, OX14 4SA, United Kingdom.

Permeate 21, now completely purified of catalyst residues by adsorption, is then fed together with the likewise adsorptively purified head product 11 to hydrogenation 14. Alternatively, it would be conceivable to feed head product 11 and permeate 21 into separate hydrogenation reactions (not depicted) instead of a conjoint hydrogenation 14.

Figure 2:
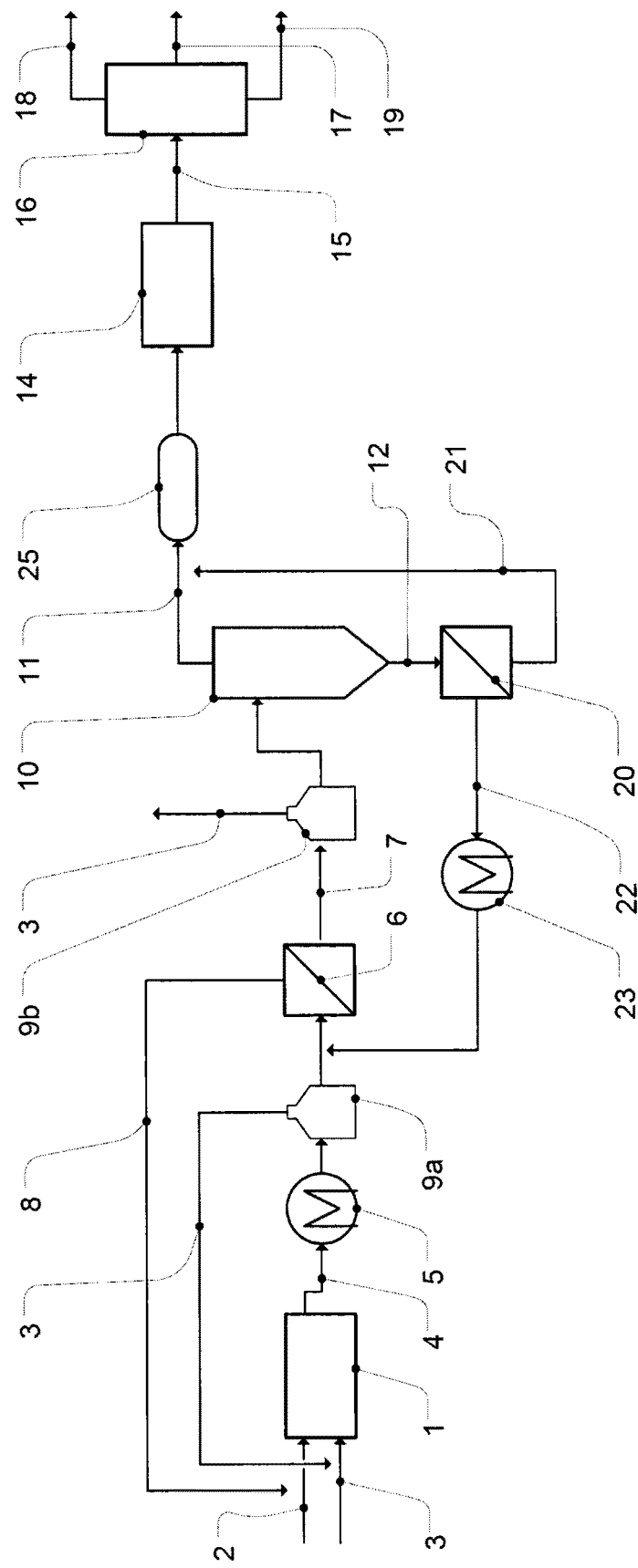

FIG. 2 shows a version of the plant of FIG. 1, where permeate 21 of the second membrane separation unit 20 and head product 11 of thermal separation unit 10 are run through a conjoint adsorber 25 and then subjected to hydrogenation 14. The use of a conjoint adsorber 25 makes it possible for less adsorbent to be used, lowering the operating costs of the plant. The operating conditions and the adsorbent in this version are chosen as just described regarding the second adsorber 24.

Figure 3:
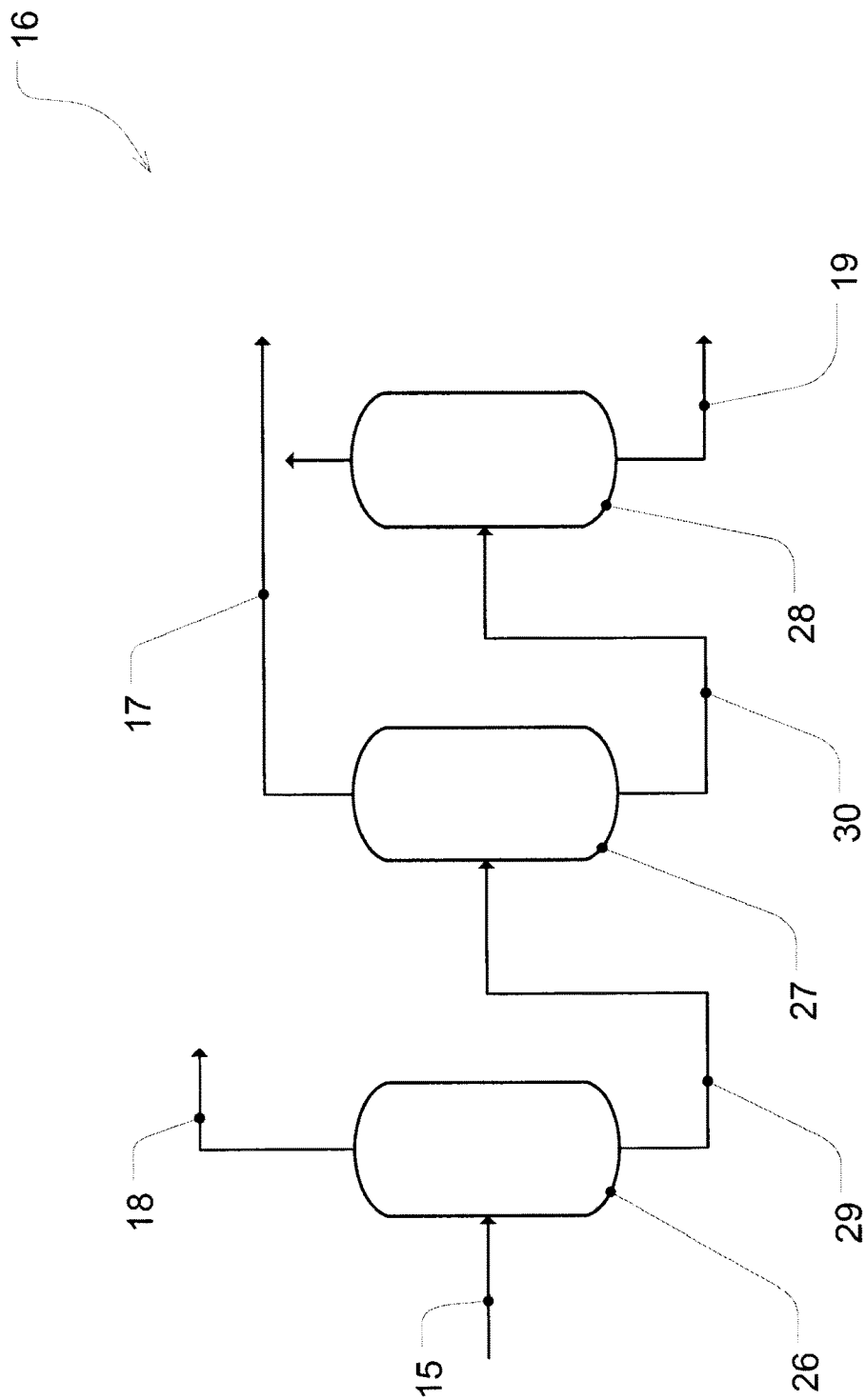

FIG. 3 shows the thermal work-up 16 in detail. It consists of a serial arrangement of three distillation columns 26, 27 and 28, which are operated at atmospheric pressure or at reduced pressure. The hydrogenation mixture 15 is fed into the first column 26. The hydrogenation mixture is separated therein into a low-boiler fraction 18, which is withdrawn overhead, and a bottom fraction 29 consisting essentially of high boilers and alcohol. The first distillation column 26 has from 20 to 70, preferably from 28 to 65 theoretical plates. The temperature in the first distillation column 26 is preferably adjusted such that the head temperature is in the range from 85 to 110° C., preferably in the range from 95 to 100° C. and the pot temperature is in the range from 175 to 200° C., preferably in the range from 185 to 193° C.

The bottom fraction 29 of the first column 26 is fed into the second distillation column 27. The alcohol-rich fraction 17 is removed therein overhead. It is preferably more than 98% target alcohol. The bottom product 30 of the second distillation column 27 is a mixture of high boilers and residual alcohol. To perform this separating duty, the second distillation column 27 has from 8 to 35, preferably from 10 to 30 theoretical plates. The temperature in the second distillation column 27 is preferably adjusted such that the head temperature is in the range from 150 to 180° C., preferably in the range from 160 to 170° C. and the pot temperature is in the range from 180 to 205° C., preferably in the range from 185 to 195° C.

The bottom product 30 of the second distillation column 27 is finally run into a third column 28 whose bottom product is the high-boiler fraction 19. Its head product comprises residual quantities of alcohol, which are mixed with the alcohol-rich fraction 17. The third distillation column 28 has from 15 to 35, preferably from 20 to 30 theoretical plates. The temperature in the third distillation column is preferably adjusted such that the head temperature is in the range from 95 to 120° C., preferably in the range from 100 to 110° C. and the pot temperature is in the range from 160 to 190° C., preferably in the range from 165 to 175° C.

The three fractions 17, 18 and 19 are removed from the system and marketed.

Figure 4:
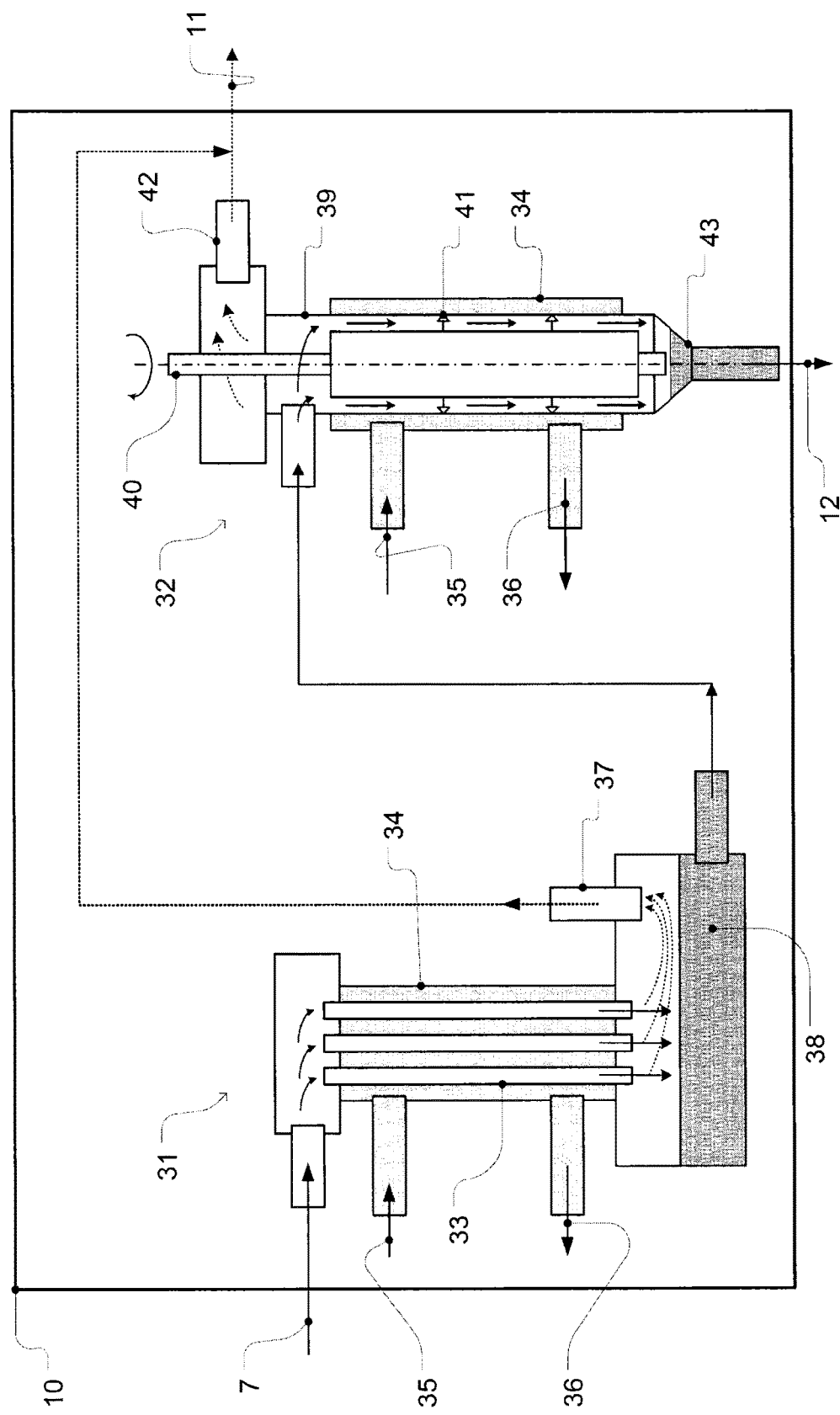

FIG. 4 shows the internal construction of thermal separation unit 10. It is formed by two serially connected thermal separation apparatuses, namely a falling film evaporator 31 and a thin film evaporator 32. The falling film evaporator 31 is of conventional technical design. The liquid product stream 7 enters at the top of the falling film evaporator 31 and is distributed from there over a multiplicity of vertically extending down pipes 33. The down pipes 33 are surrounded by a heating jacket 34 heated with medium pressure vapour. The medium pressure vapour is water vapour used as heating medium which does not react with the process chemicals. Its pressure is between 1.2 and 2.4 MPa, depending on site conditions. The medium pressure vapour enters heating jacket 34 through a steam inlet 35, passes its heat via the walls of down pipes 33 to product stream 7 and exits again via a steam outlet 36, having cooled down. The liquid product stream 7 passes downwardly through the down pipes 33 in line with the force of gravity and in the course of its passage is heated up by the hot steam (about 120° C.). At the point of exit at the base of the down pipes 33, the components of the product stream 7 which boil at 120° C. are very largely evaporated. It must be borne in mind here that a negative pressure of 3 and 500 hPa prevails in falling film evaporator 31. The evaporated fractions of product stream 7 depart the falling film evaporator 31 via a gas exit 37. The components which have not evaporated collect in the bottom product 38 and pass from there into the thin film evaporator 32.

The thin film evaporator 32 is similar to the falling film evaporator 31 in having a medium pressure vapour heated heating jacket 34 wherethrough the process steam flows in through a steam inlet 35 and departs again through a steam outlet 36, having cooled down. The steam heats a beak 39 from the outside, the inside surface of which is a support for the hitherto unvaporized fractions of product stream 7 from bottom product 38 of falling film evaporator 31. A rotor 40 is arranged coaxially within the beak 39 and turns about the longitudinal axis of thin film evaporator 32. It is equipped with a multiplicity of wipers 41, which spread the liquid feed into a thin film on the inside surface of beak 39. The fractions which evaporate in the process depart the thin film evaporator 32 via a gas exit 42 and are then combined with the evaporated components from falling film evaporator 31 (ex gas exit 37) to form the head product 11 of the thermal separation unit 10. In this way, about 90% of the mass introduced into the thermal separation unit 10 with product stream 7 is evaporated and withdrawn as head product 11.

The remaining 10% of the introduced product stream 7 depart the thermal separation unit 10 in liquid form, namely from the base 43 of the thin film evaporator, where the fractions of the feed of the thin film evaporator 32 which have not evaporated within beak 39 collect. Bottom product 43 accordingly corresponds to bottom product 12 of thermal separation unit 10.

Figure 5:
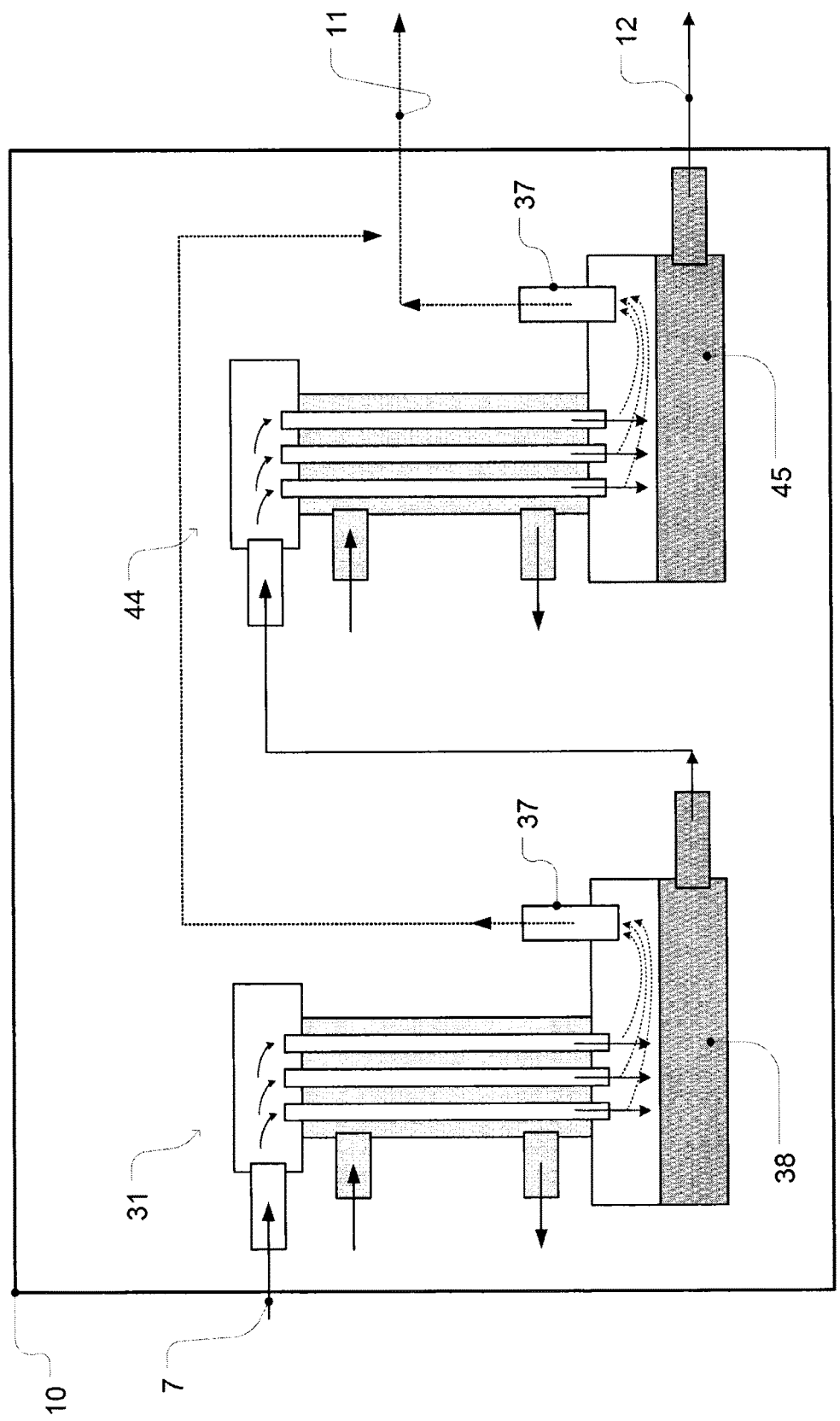

FIG. 5 depicts an alternative embodiment of thermal separation unit 10. It consists of two serially connected falling film evaporators 31 and 44. The two falling film evaporators 31 and 44 correspond to the falling film evaporator 31 shown in FIG. 4 and therefore need not be further elucidated. Their respective gas exits 37 are combined to form the head product 11 of thermal separation unit 10. The bottom product 12 of thermal separation unit 10 is withdrawn from the base 45 of the second falling film evaporator 44. The bottom product 38 of the first falling film evaporator 31 serves as feed to the second falling film evaporator 44. The same method can be used to serially connect three falling film evaporators (not depicted).

Figure 6:
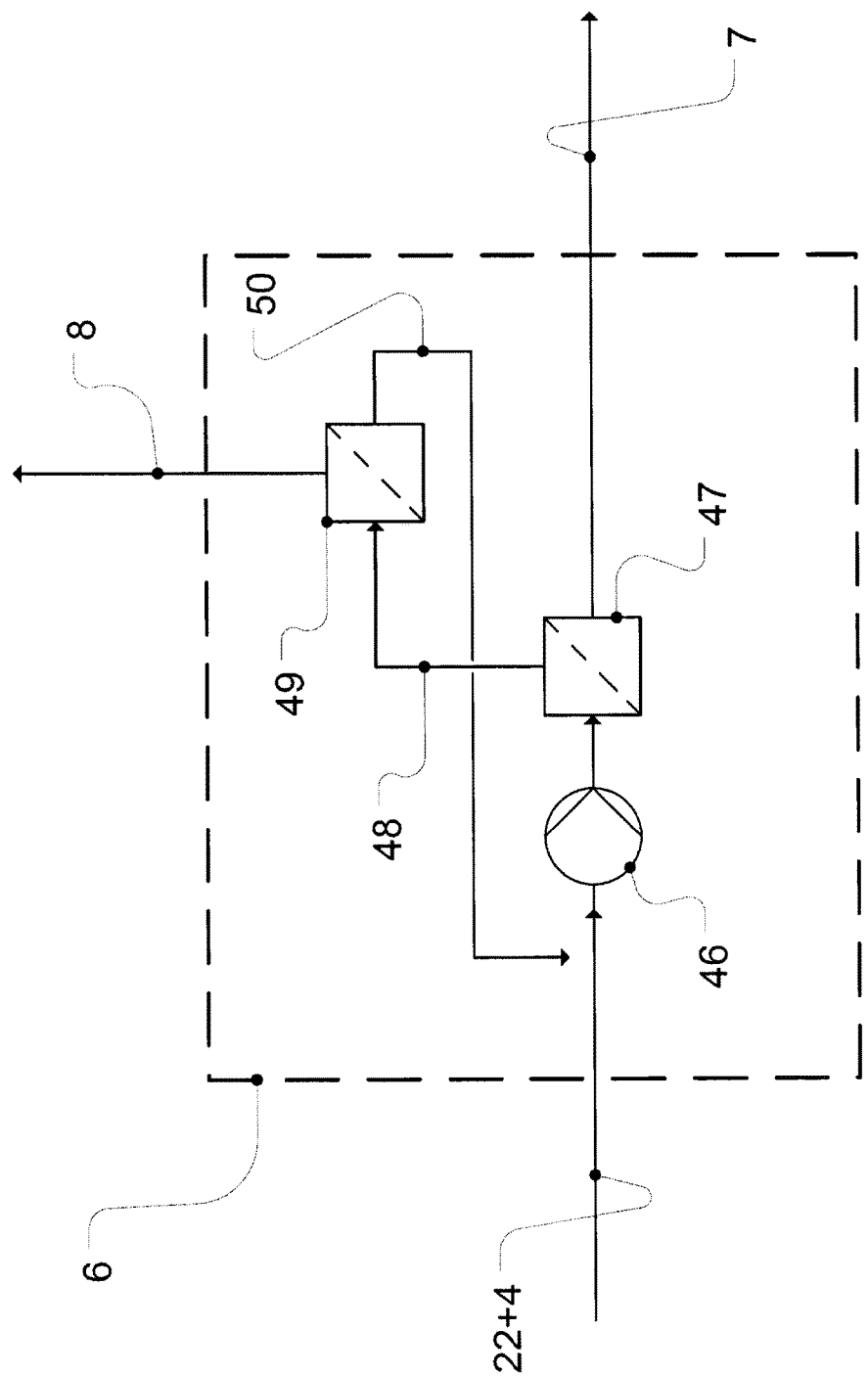

FIG. 6 shows the in-principle construction of first membrane separation unit 6. The first membrane separation unit 6 is a two-stage depleting cascade. It is fed with a mixture of the devolatilized hydroformylation effluent 4 of the reactor and retentate 22 of the second membrane separation stage by means of a pump 46 of a first stage 47. The permeate of the first stage 47 corresponds to the resulting permeate of the first membrane separation unit 6 and hence to product stream 7 of the plant. The retentate 48 of the first stage 47 is applied to a second stage 49 without further increase in pressure. The retentate 8 of the second stage 49 corresponds to the resulting retentate of the first membrane separation unit 6 and is recycled as reactor return stream 8 to a point upstream of hydroformylation reactor 1. The permeate 50 of the second stage 49 is mixed with the feed of the first membrane separation unit and fed via pump 46 back to the first stage 47. The permeate 50 of the second stage 49 thus corresponds to the internal permeate recycle of the membrane separation unit configured as a depleting cascade.

Figure 7:
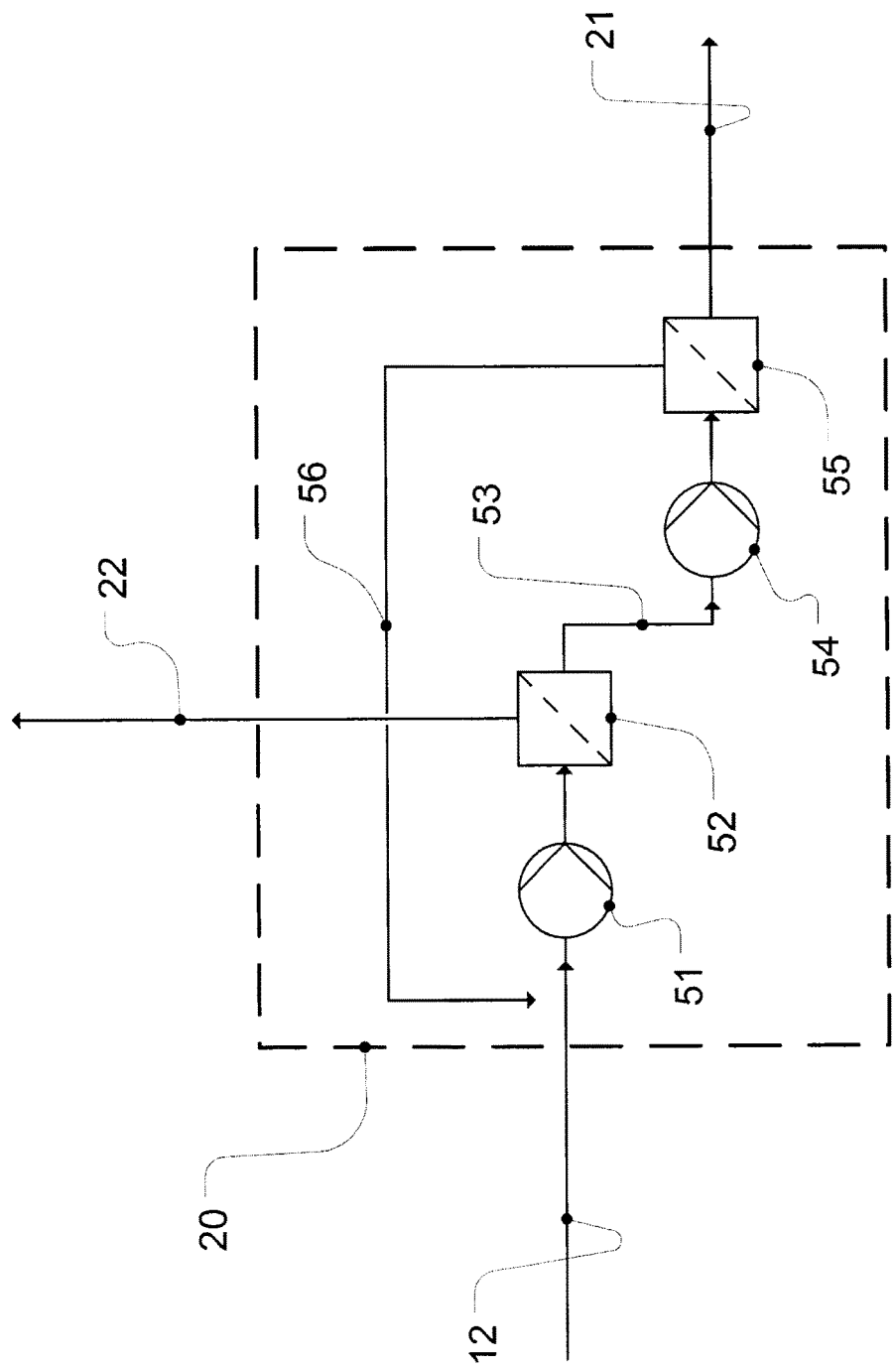

FIG. 7 shows the internal construction of the second membrane separation unit 20. It is configured as a two-stage enriching cascade. The feed for the second membrane separation unit 20 is the bottom product 12 of the thermal separation unit 10. It is compressed by a first pressure elevation pump 51 to a pressure of about 3 MPa and applied to a first stage 52. The retentate of the first stage 52 corresponds to the resulting retentate of the second membrane separation unit 20 and departs the second membrane separation stage 20 as retentate 22/secondary recyclate and is mixed with the devolatilized hydroformylation effluent 40 and returned in this form into the first membrane separation unit 6.

The permeate 53 of the first stage 52 is again brought by a second pressure elevation pump 54 to a pressure of about 3 MPa in order that the transmembrane pressure of the first stage 52 may be equalized. The second stage 55 of the membrane separation system then ensues. The resulting permeate 21 corresponds to the resulting permeate 21 of the second membrane separation unit 20. It is subjected to adsorptive purification and then subjected to hydrogenation. The retentate 56 of the second stage 55 is mixed with the feed of the second membrane separation stage 20 (=bottom product 12) and returned via the first pressure elevation pump 51 into the first stage 52. The retentate 56 of the second stage thus constitutes the internal retentate recycle of the enriching cascade.

EXAMPLES

Variants of working under the hydroformylation effluent in the manner of the present invention will now be compared by means of simulations. Simulation is the means of choice because of the complexity of the plant structure.

The process under consideration is the production of $C_9$ alcohols from $C_8$ olefins.

Model of Hydroformylation

The simulation describes the hydroformylation of the $C_8$ olefin mixture dibutene in simplified form via a formally kinetic approach. The following reactions were taken into account. The main reaction is the hydroformylation of dibutene with synthesis gas (CO+H2) to form the $C_9$ aldehyde nonanal (INAL) as per reaction 1:

dibutene+CO+H2→INAL    Reaction 1:

The further reaction taken into account is descendant reaction 2, the hydrogenation of the aldehyde INAL to the alcohol isononanol (INA):

INAL+H2→INA    Reaction 2:

A particular point of interest in simulating this hydroformylation process, which employs nanofiltration, is how possible high boilers build up in the catalyst circuit. But high-boiler formation involves a multiplicity of unknown reactions. To keep the reaction system as simple as possible, therefore, the kinetic model only takes account of one further reaction to model high-boiler formation. Accordingly, there is only one high-boiling component in the simulation to represent the actual high-boiler mixture formed in the course of the hydroformylation. The high boilers are represented by dinonyl ether (DiEther) in the simulation. Dinonyl ether is formed as per reaction 3 from nonanal (INAL) and nonanol (INA):

INA+INAL+H2→H2O+DiEther    Reaction 3:

In principle, the selection of the high-boiler reaction is arbitrary. The ether formation in reaction 3 can thus also be replaced by some other reaction in which no water (H2O) is formed, an acetal formation for example.

To map the dependencies of the reactions on the various quantities, the following equations were employed to model the reaction rates (in kmol m$^{-3}$ min$^{-1}$) $r_i$, i=1, . . . , 3:

$$r_1 = c_{total} k_1 \left( x_{dibutene}^{n_1} - \left( \frac{x_{nonanal}}{k_{ggw} p^2} \right)^{n_1} \right) c_{Rh}^{n_{Rh}} k_{Li} k_p \quad (1)$$

$$r_2 = c_{total} k_2 x_{nonanal} c_{Rh}^{n_{Rh}} \quad (2)$$

$$r_3 = c_{total} k_3 x_{nonanal} x_{nonanol} \quad (3)$$

where $c_{total}$ is the total amount of substance concentration [kmol/m$^3$], $x_i$ is the molar fraction of component i, p is the pressure in bar, and $c_{Rh}$ is the Rh concentration in ppm. The dependence on the Rh concentration is mapped via the exponent nRh; $n_1$ is the order of the first reaction. The reaction rate $k_i$ is modelled using the Arrhenius approach:

$$k_i = k_{0,i} \exp\left( -\frac{E_{Ai}}{RT} \right) \quad (4)$$

The term $k_{Li}$ is used to represent the dependence of the hydroformylation reaction R1 on the ratio between ligand and rhodium.

$$k_{Li} = 1 + \frac{k_{Li,1} X_{Li}}{1 + k_{Li,2} X_{Li}^2} \quad (5)$$

$X_{Li}$ is the molar ratio between ligand and rhodium. The pressure dependence $k_p$ is represented by:

$$k_p = \tan h(k_{p,0} p) \quad (6)$$

Finally, the constant $k_{ggw}$ is used to describe the (pseudo) equilibrium between dibutene and nonanal. The values of all the constants are summarised in Table 1.

TABLE 1

Values of constant reaction parameters

| Parameter | Value | Parameter | Value |
|---|---|---|---|
| $k_{0,1}$ | 13537 min$^{-1}$ | $E_{A,1}$ | 56037 kJ/kmol K |
| $k_{0,2}$ | 26810 · 10$^3$ min$^{-1}$ | $E_{A,2}$ | 92703 kJ/kmol K |
| $k_{0,3}$ | 1840 min$^{-1}$ | $E_{A,3}$ | 50858 kJ/kmol K |
| $k_{Li,1}$ | 2.453 | $k_{Li,2}$ | 0.01342 |
| $k_{P,0}$ | 0.004975 bar$^{-1}$ | $k_{ggw}$ | 0.0601 bar$^{-2}$ |
| $n_1$ | 1.452 | $n_{Rh}$ | 0.6 |

The hydroformylation reaction (R1) is actually not an equilibrium reaction. However, autoclave test results have shown that complete dibutene conversion is not attained by the end of a 6 h run. A possible explanation for this is that the less speedily reacting di-methylhexene isomers have still not been completely converted by the end of the runs. However, the simple model of the formal kinetics which is used here does not distinguish between the various dibutenes. Introduction of a pseudo equilibrium between dibutene and nonanal is a way to describe the incomplete conversion. The square pressure dependence in equation (1) follows from the pseudo equilibrium condition:

$$k_{ggw}^* = \frac{x_{nonanal,ggw}}{x_{dibutene,ggw} x_{CO,ggw} x_{H_2,ggw}} \approx \qquad (7)$$

$$a \frac{x_{nonanal,ggw}}{x_{dibutene,ggw} p_{CO} p_{H_2}} \approx a^* \frac{x_{nonanal,ggw}}{x_{dibutene,ggw} p^2}, k_{ggw} = \frac{k_{ggw}^*}{a^*}$$

Only the square pressure dependence of the equilibrium term allows for satisfactory kinetic modelling of the experimental results at varying pressure.

Model of Organophilic Nanofiltration (Membrane Separation)

Organophilic nanofiltration through a membrane is mapped by a simple model for the purposes of the simulation. In this model, the transmembrane flux is computed as a function of the temperature, of the transmembrane pressure and of the composition on the retentate side and on the permeate side. The simplified approach which forms the basis of the model does not compute any locally distributed concentration profile and neglects the pressure drop in the flow across the membrane. The assumption that the composition—and hence also the driving concentration difference—across the full membrane area is the same as at the membrane exit point causes the model to underestimate the separation effect of the membrane and to overestimate the area. Owing to the simplicity of its equations, however, the membrane module is useful for an initial screening of the various versions of the process by simulation. A simplified model of membrane separation as organophilic nanofiltration is shown by FIG. 8.

Figure 8:
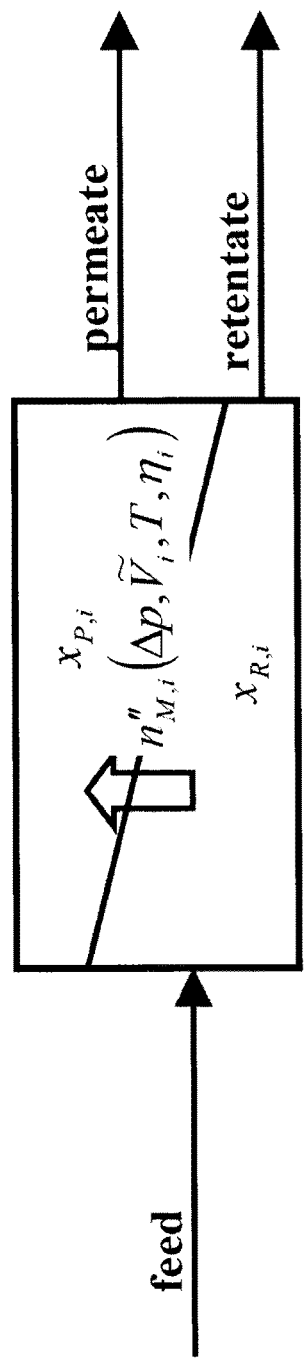
FIG. 8 shows a simplified model of organophilic nanofiltration for calculating membrane separation.

FIG. 8: Simplified model of organophilic nanofiltration

The molar permeate flux $n''_{M,i}$ of component i (see FIG. 8) is computed in the model via the pure component flux $n''_{M,i,pure}$:

$$n''_{M,i,pure} = P_{i,p}^0 \cdot \exp(-\alpha_{i,p} \Delta p) \Delta p \frac{\eta_{i,pure}(T_{Ref})}{\eta_{i,pure}(T) M_i} \qquad (8)$$

Here $P_{i,p}0$ is the standard permeance (mass specific) of the membrane for component i at a transmembrane pressure of 0 bar. The parameter $\alpha_{i,p}$ describes the compacting of the membrane, $\Delta p$ is the transmembrane pressure and $\eta_{i,pure}$ is the viscosity of the pure material and Mi is its molar weight. The pure component flux and the molar volume $\tilde{V}i$ is used to compute the permeance of the membrane, $$P_{i,p} = n''_{M,i,pure} / 1 - \left(\exp\left(\frac{-\Delta p \tilde{V}_i}{RT}\right)\right) \qquad (9)$$

The permeance can finally be used to determine the permeate flux $n''_{M,i}$:

$$n''_{M,i} = P_{i,p} \cdot \left(x_{R,i} - x_{P,i} \exp\left(\frac{-\Delta p \tilde{V}_i}{RT}\right)\right) \qquad (10)$$

Table 2 shows the standard permeances for the simulation:

TABLE 2

Standard permeances

| Material | Permeance ONF 2 |
|---|---|
| Dibutene | 0.074 kg h$^{-1}$ m$^{-2}$ |
| Nonanal | 0.140 kg h$^{-1}$ m$^{-2}$ |
| Nonanol | 0.150 kg h$^{-1}$ m$^{-2}$ |
| High boiler | 0.105 kg h$^{-1}$ m$^{-2}$ |
| Complex | 0.026 kg h$^{-1}$ m$^{-2}$ |
| Ligand | 0.099 kg h$^{-1}$ m$^{-2}$ |

There are various factors affecting the economics of the process. For one, the rhodium consumption factor (corresponds to the loss of Rh) should be very low; for another, the capital costs—inter alia dependent on the membrane area needed—should not be too high.

In the variants under consideration, the overall volume of the reactor is 67 m$^3$. Aspects such as heat transfer or the geometry of the reactor were left out of the modelling. The dibutene feed is 20 t/hr, so presuming an annual on-stream time of 8500 hours a yield of 93% for conversion into the product nonanal is needed to attain the world scale standard of 200 kt/a. This yield is unattainable with a dibutene residual content of 8%, so recycling of the unreacted dibutenes is required in this case. This is taken into account in the simulation computations regarding interconnection variants A to D. The membrane stages all employed the oNF2 from GMT Membrantechnik GmbH. Employing other membranes in the entire plant or else only in parts of the plant might further improve the economics.

Membrane temperature is 33° C. in the simulation computations regarding interconnection variants A to D. Higher operating temperatures for the nanofiltration reduce the membrane area while at the same time the membrane retention for the catalyst system decreases faster over time. Depending on membrane replacement costs, higher operating temperatures may be more economical in order to reduce total installed membrane area. Transmembrane pressure difference for the simulations performed is 35 bar (3.5 MPa).

Four operative variants A to D of the invention will now be more particularly investigated:

Interconnection Variant A

Owing to the high rhodium losses in the nonanal product stream in a purely membrane-based separation, the high boiler and the remaining rhodium are hereinbelow separated from the nonanal stream downstream of the first membrane separation stage (NF1) by a thermal separation unit in the form of a thin film evaporator (DSV). This is depicted in FIG. 9.

Figure 9:
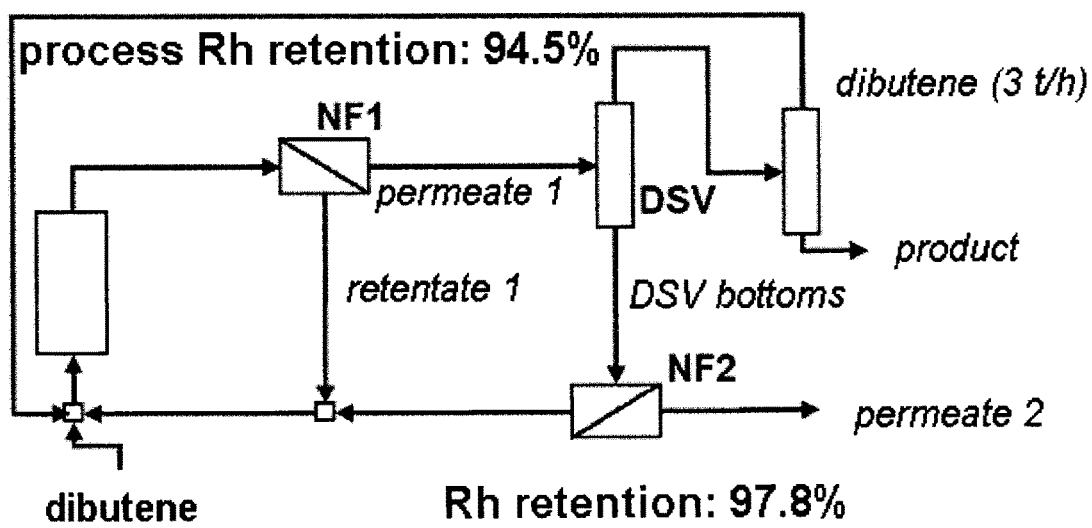
FIG. 9 shows a depiction of a membrane separation cascade for Variant A according to an embodiment of the invention.

FIG. 9: Interconnection variant A

Owing to the small rhodium concentration in the permeate, the thermal separation leads to a small loss of rhodium due to clustering. This rhodium loss is left out of the simulation.

As a result of the thermal separation, the high boilers build up in the catalyst circuit. A portion of the high boiler stream is therefore separated off via a second membrane separation unit (NF2) in order to avoid an excessive build-up in the concentration of high boiler in the catalyst circuit. The further processing of the high boiler export, which is of interest by reason of the still considerable nonanal concentration, is not further considered in the simulation. After removal of the high boiler, the unreacted dibutene, which still comprises ~7% of the product stream, is separated off and returned into the reactor in order to achieve full conversion for the dibutene and attain the required nonanal production of 200 kta. The thermal reprocessing of the product mixture is modelled in the simulation as a simple splitter featuring fixed splitting factors. The first separating step is a flash evaporator operated at 40 mbar. The evaporator setting is established to ensure that 98% of the high boiler remains in the bottom product.

Table 3 shows the results of the simulation. The computed membrane areas are 2416 m$^2$ and 384 m$^2$ for the first membrane separation unit and the second membrane separation unit, respectively. The rhodium consumption factor is 0.145 g of rhodium per metric ton (t) of nonanal. Of this, 38.9% is removed via the permeate from the second membrane separation unit. It is simple to further reduce this fraction by means of an adsorber or a further nanofiltration stage. The remaining 61.1% are losses due to clustering and segregation within the plant. The bottom product of the thermal separation unit DSV in this interconnection has a lower rhodium concentration than the retentate of the first membrane separation unit. The proportion accounted for by clustering is comparatively high.

TABLE 3

Results of interconnection variant A

|  | Permeate 1 | Retentate 1 | Bottoms | Permeate 2 |
| --- | --- | --- | --- | --- |
| Rate [t/h] | 30.1 | 1.2 | 2.8 | 0.4 |
| Dibutene [wt %] | 10.5% | 6.4% | 1.1% | 0.8% |
| Nonanal [wt %] | 82.7% | 47.3% | 45.5% | 51.4% |
| Nonanol [wt %] | 2.1% | 1.3% | 3.9% | 4.4% |
| High boiler [wt %] | 4.7% | 45.0% | 49.5% | 43.4% |
| Rhodium [ppm] | 12.2 | 222.1 | 130.9 | 3.3 |

Interconnection Variant B

In variant B, the bottom product of the thermal separation unit (DSV) is routed to a point upstream of the first single-stage membrane separation unit (NF1). The high boilers are exported by feeding the retentate of the first membrane separation unit (NF1) to the second two-stage membrane separation unit (enrichment cascade NF2). This interconnection is depicted in FIG. 10.

Figure 10:
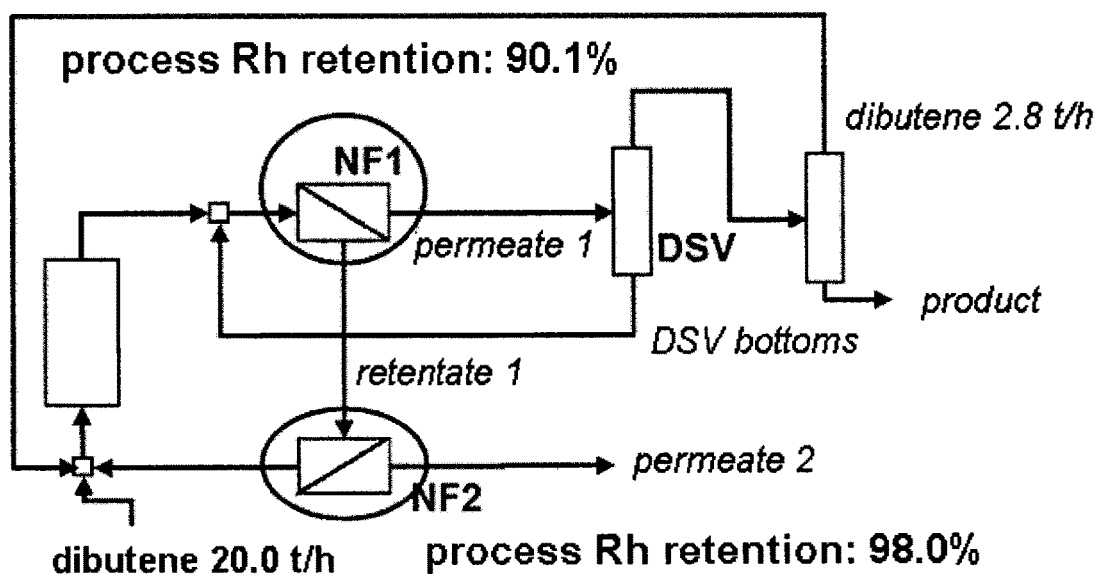
FIG. 10 shows a depiction of a membrane separation cascade for Variant B according to an embodiment of the invention.

FIG. 10: Interconnection variant B

Table 4 shows the results of the simulation. The computed membrane areas are 3032 m$^2$ and 392 m$^2$ for the first membrane separation unit and the second membrane separation unit, respectively. The rhodium consumption factor is 0.144 g of rhodium per metric ton of nonanal. Of this, 40.3% is removed via the permeate from the second nanofiltration. It is simple to further reduce this proportion by means of a scavenger or a further nanofiltration stage. The remaining 59.7% are losses due to clustering and segregation within the plant.

TABLE 4

Results of interconnection variant B

|  | Permeate 1 | Retentate 1 | Bottoms | Permeate 2 |
| --- | --- | --- | --- | --- |
| Rate [t/h] | 30.9 | 4 | 3.7 | 0.4 |
| Dibutene [wt %] | 9.7% | 6.4% | 1.0% | 6.3% |
| Nonanal [wt %] | 80.8% | 50.5% | 36.2% | 56.9% |
| Nonanol [wt %] | 2.2% | 1.4% | 3.3% | 1.6% |
| High boiler [wt %] | 7.3% | 41.6% | 59.5% | 35.3% |
| Rhodium [ppm] | 15.5 | 157 | 129.4 | 3.5 |

Interconnection Variant C

Figure 11:
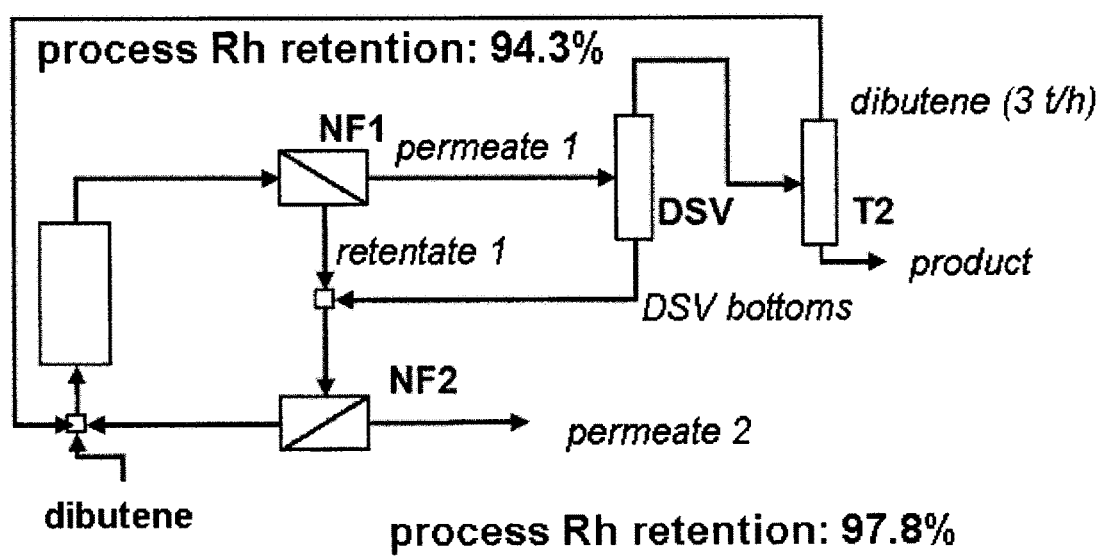
FIG. 11 shows a depiction of a membrane separation cascade for Variant C according to an embodiment of the invention.

Interconnection variant C is depicted in FIG. 11. The retentate of the first membrane separation unit (NF1) and the bottom product of the thermal separation unit (DSV) are mixed at a point upstream of the second membrane separation unit (NF2) and this mixture is run into the second membrane separation unit for high boiler exportation. In order that a catalyst cycle of 4 t/h may continue to be maintained, the retentate rate of the first membrane separation unit was reduced to 1.2 t/h. The retentate of the second membrane separation stage is recycled to upstream of the reactor.

FIG. 11: Interconnection variant C

Table 5 shows the results of the simulation. The computed membrane areas are 2473 m$^2$ and 388 m$^2$ for the first nanofiltration and the second nanofiltration, respectively. The rhodium consumption factor is 0.152 g of rhodium per metric ton of nonanal. Of this, 42.1% is removed via the permeate from the second nanofiltration. It is simple to further reduce this proportion by means of a scavenger or a further nanofiltration stage. The remaining 57.9% are losses due to clustering and segregation within the plant.

TABLE 5

Results of interconnection variant C

|  | Permeate 1 | Retentate 1 | Bottoms | Permeate 2 |
| --- | --- | --- | --- | --- |
| Rate [t/h] | 30.2 | 1.2 | 2.9 | 0.4 |
| Dibutene [wt %] | 10.5% | 6.4% | 1.1% | 2.4% |
| Nonanal [wt %] | 82.4% | 46.6% | 44.3% | 51.1% |
| Nonanol [wt %] | 2.1% | 1.2% | 3.8% | 3.5% |
| High boiler [wt %] | 5.0% | 45.8% | 50.8% | 43.0% |
| Rhodium [ppm] | 12.4 | 217.8 | 129.6 | 3.8 |

Interconnection Variant D

Figure 12:
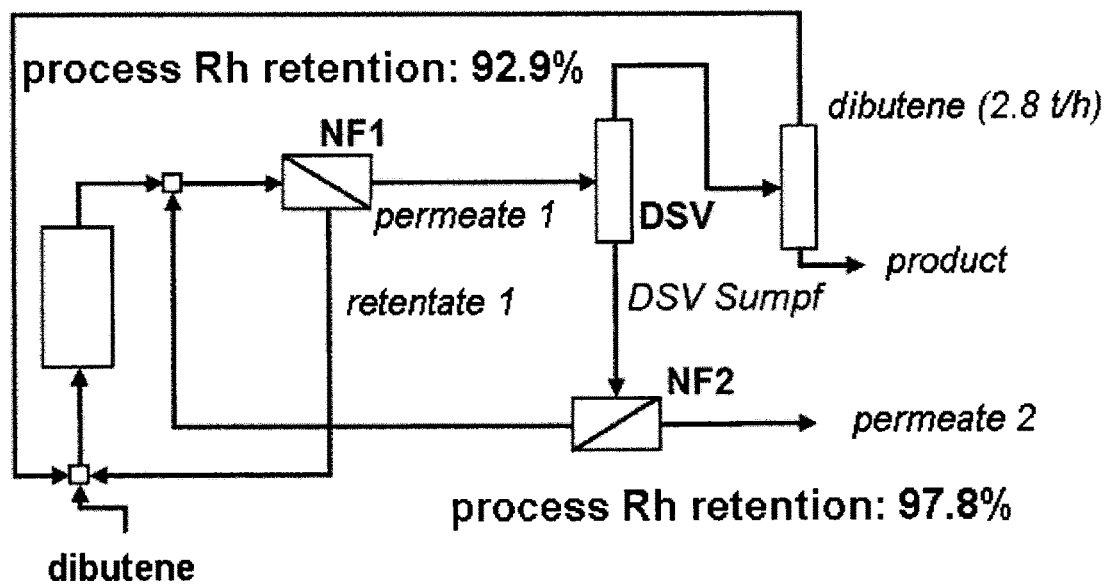
FIG. 12 shows a depiction of a membrane separation cascade for Variant D according to an embodiment of the invention.

Interconnection variant D as depicted in FIG. 12 shows a mode wherein, as in the case of variant A, the bottom product of the thermal separation means (DSV) is fed to the second membrane separation unit (NF2) for the purpose of high boiler exportation. However, the retentate of the second membrane separation unit is mixed with the hydroformylation effluent and fed to the first membrane separation unit and not, as in the case of variant C, returned to a point upstream of the reactor.

FIG. 12: Interconnection variant D

Table 6 shows the results of the simulation. The computed membrane areas are 2324 m$^2$ and 382 m$^2$ for the first membrane separation unit (NF1) and the second membrane separation unit (NF2), respectively. The rhodium consumption factor is 0.138 g of rhodium per metric ton (t) of nonanal. Of this, 37.7% is removed via the permeate from the second membrane separation unit. It is simple to further reduce this fraction by means of an adsorber or a further nanofiltration stage.

The remaining 62.3% are losses due to clustering and segregation within the plant. The concentration in the bottom product of the thermal separation unit is lower than in the retentate of the first membrane separation unit, leading to a reduced level of clustering. In addition, a larger retentate stream can be run in the first membrane separation unit than in the case of interconnections A and C.

TABLE 6

Results of interconnection variant D

|  | Permeate 1 | Retentate 1 | Bottoms | Permeate 2 |
|---|---|---|---|---|
| Rate [t/h] | 29.9 | 4 | 2.7 | 0.4 |
| Dibutene [wt %] | 10.1% | 7.3% | 1.1% | 0.8% |
| Nonanal [wt %] | 83.3% | 57.7% | 47.4% | 53.3% |
| Nonanol [wt %] | 2.2% | 1.6% | 4.1% | 4.7% |
| High boiler [wt %] | 4.3% | 33.4% | 47.4% | 41.2% |
| Rhodium [ppm] | 11.3 | 159.3 | 125.4 | 3.1 |

Conclusion

FIGS. 13 to 16 give a graphic juxtaposition of the results of simulated interconnection variants A to D.

Figure 13:
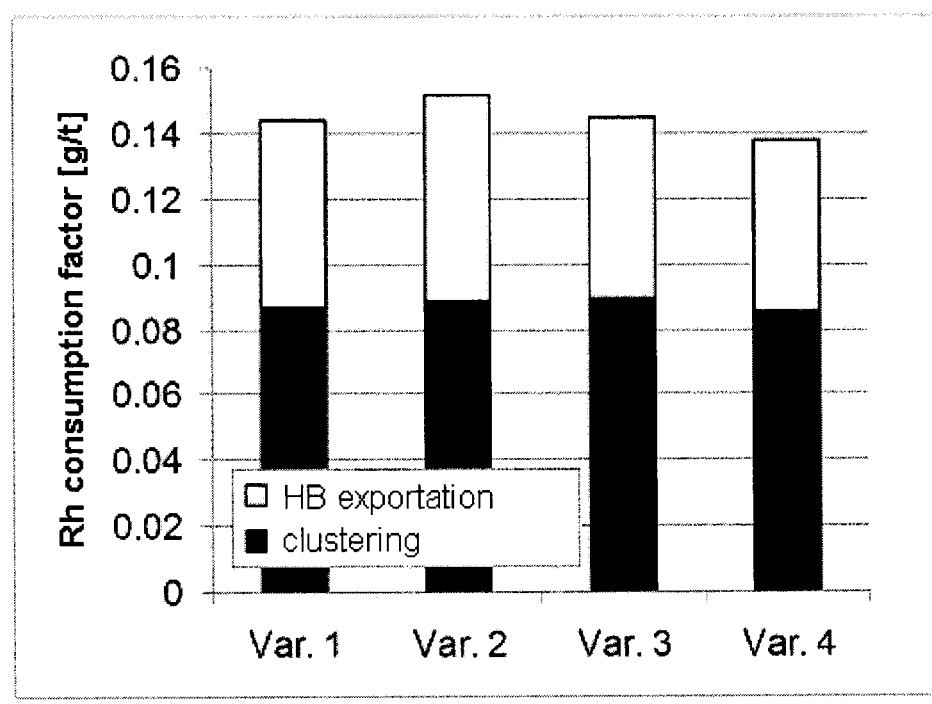
FIG. 13 shows a comparison of results of simulation computations with respect to the Rh consumption factor.
Figure 14:
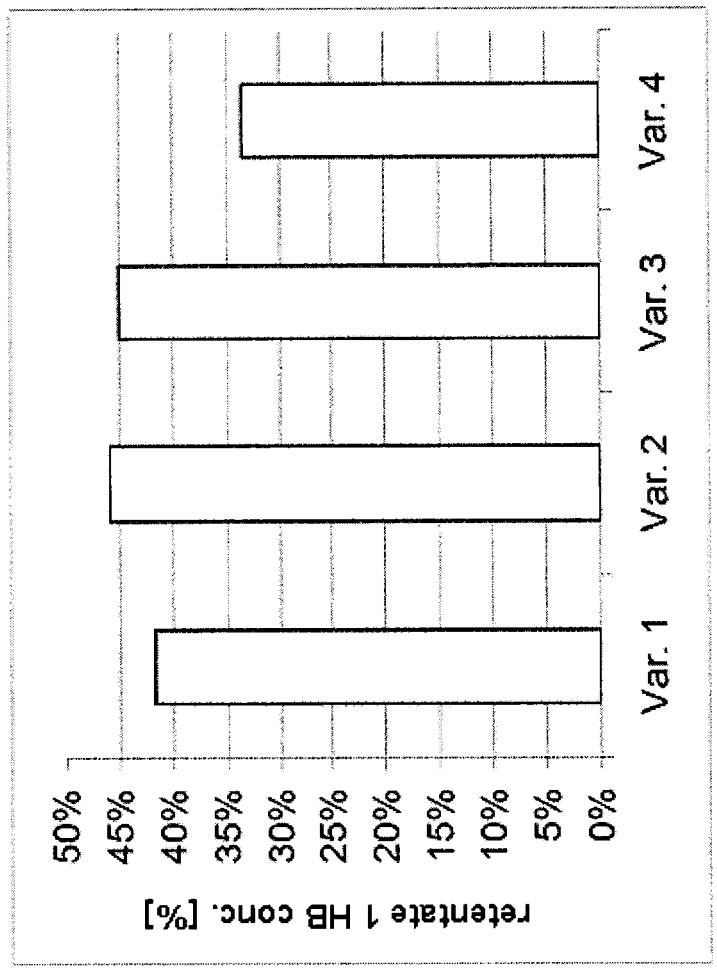
FIG. 14 shows a comparison of results of simulation computations with respect to the high boiler concentration in the retentate.
Figure 15:
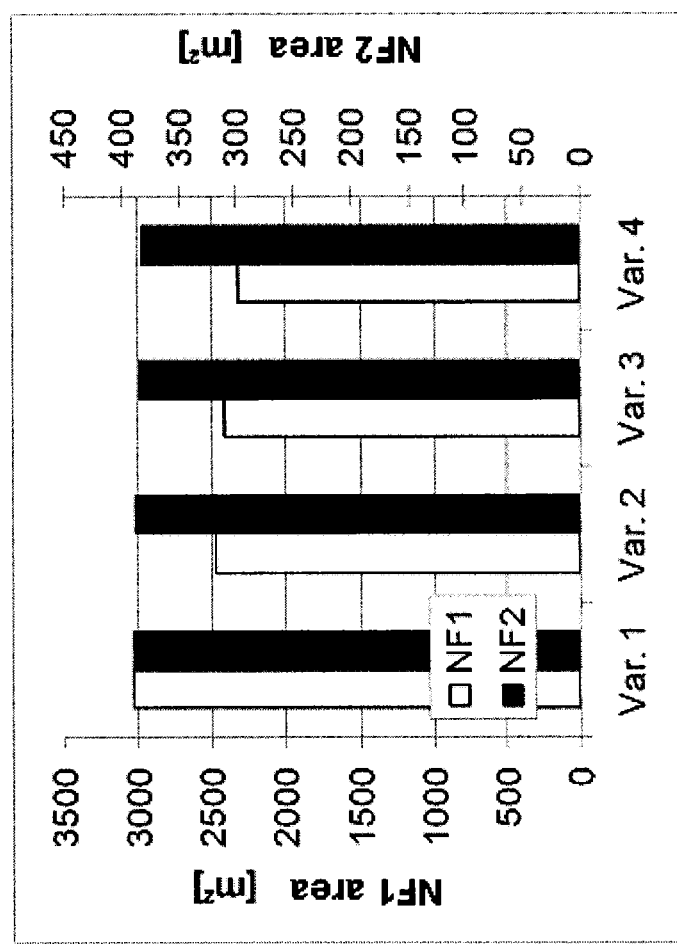
FIG. 15 shows a comparison of results of simulation computations with respect to the membrane area requirements.
Figure 16:
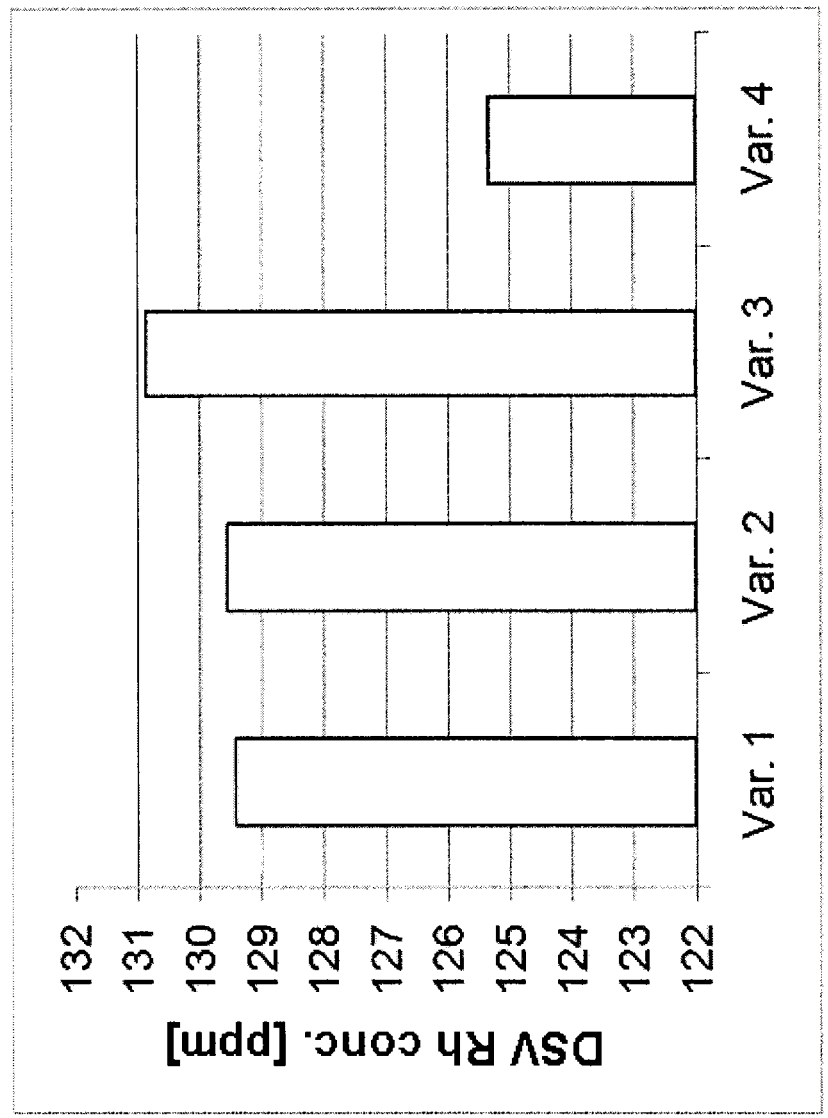
FIG. 16 shows a comparison of results of simulation computations with respect to the rhodium concentration in the separation unit.

FIG. 13: Comparison of results of simulation computations in respect of Rh consumption factor;

FIG. 14: Comparison of results of simulation computations in respect of the high boiler concentration in the retentate;

FIG. 15: Comparison of results of simulation computations in respect of the membrane area requirements;

FIG. 16: Comparison of results of simulation computations in respect of the rhodium concentration in the separation unit.

Comparing the graphic depiction in FIGS. 13 to 16 shows that variant D is the most favourable one with respect to all the parameters relevant to the economics of product removal. Variant D allows the smallest rhodium losses due to exportation and clustering and also has the lowest membrane area requirements.

Of all invention embodiments A to D, therefore, the interconnection variant D—characterized by returning the retentate of the second membrane separation stage to a point upstream of the first membrane separation stage—is the preferred one.

LIST OF REFERENCE SIGNS 1 hydroformylation reactor
2 olefin
3 syngas
4 hydroformylation effluent
5 first heat exchanger
6 first membrane separation unit
7 product stream
8 reactor return stream/primary recycle
9 devolatilizer
10 thermal separation unit
11 head product
12 bottom product
13 first adsorber
14 hydrogenation
15 hydrogenation mixture
16 thermal work-up
17 alcohol-rich fraction
18 low-boiler fraction
19 high-boiler fraction
20 second membrane separation unit
21 permeate
22 retentate/secondary recyclate
23 second heat exchanger
24 second adsorber
25 conjoint adsorber
26 first distillation column
27 second distillation column
28 third distillation column
29 bottom product of first distillation column
30 bottom product of second distillation column
31 falling film evaporator
32 thin film evaporator
33 down pipes
34 heating jacket
35 steam inlet
36 steam outlet
37 gas exit from falling film evaporator
38 base of falling film evaporator
39 beak
40 rotor
41 wipers
42 gas exit from thin film evaporator
43 base of thin film evaporator
44 second falling film evaporator
45 base of second falling film evaporator
46 pump of depleting cascade
47 first stage of depleting cascade
48 retentate of first stage of depleting cascade
49 second stage of depleting cascade
50 permeate of second stage of depleting cascade/permeate recycle
51 first pressure elevation pump of enriching cascade
52 first stage of enriching cascade
53 permeate of first stage of enriching cascade
54 second pressure elevation pump of enriching cascade
55 second stage of enriching cascade
56 retentate of second stage of enriching cascade/retentate recycle

The invention claimed is:

1. A process for producing an alcohol, the process comprising:
   a) providing at least one olefin, syngas and a catalyst system and optionally a solvent;
   b) hydroformylating the olefin in the presence of the syngas and of the catalyst system in at least one hydroformylation reactor in a homogeneously catalysed hydroformulation to form at least one aldehyde and at least one high boiler;
   c) withdrawing a liquid hydroformylation effluent comprising the aldehyde, the olefin, dissolved syngas, the catalyst system and the high boiler from the hydroformylation reactor;
   d) optionally devolatilizing the liquid hydroformylation effluent;
   e) separating the liquid hydroformylation effluent in a first membrane separation unit into a product stream and a reactor return stream, wherein the catalyst system partitions into the reactor return stream;
   f) returning the reactor return stream into the hydroformylation reactor;
   g) optionally devolatilizing the product stream;

h) separating the product stream in a thermal separation unit into a gaseous head product comprising a first part of the aldehyde and the olefin and a liquid bottom product comprising a second part of the aldehyde, the high boiler and a catalyst complex; and i) separating the liquid bottom product in a second membrane separation unit into a permeate and a retentate, wherein the catalyst system partitions into the retentate; and wherein an improvement of the process comprises:

(j) operating the thermal separation unit such that 80% to 98% of mass introduced into the thermal separation unit with the product stream re-emerges from the thermal separation unit as head product;

(k) subjecting at least some of the head product of the thermal separation unit and the permeate of the second membrane separation unit to conjoint or separate hydrogenation; and (l) the second membrane separation unit takes a form of a two-stage enriching cascade.

2. The process according to claim 1, wherein the retentate of the second membrane separation unit is fed to the first membrane separation unit in admixture with the liquid hydroformylation effluent withdrawn from the hydroformylation reactor.

3. The process according to claim 1, wherein the permeate of the second membrane separation unit passes through an adsorber before the hydrogenation.

4. The process according to claim 1, wherein the head product of the thermal separation unit passes through an adsorber before the hydrogenation.

5. The process according to claim 3, wherein the head product of the thermal separation unit and the permeate of the second membrane separation unit pass through the same adsorber before the hydrogenation.

6. The process according to claim 5, wherein the head product of the thermal separation unit and the permeate of the second membrane separation unit are subject to the conjoint hydrogenation.

7. The process according to claim 1, wherein a hydrogenation mixture is withdrawn from the hydrogenation and subjected to a thermal work-up to obtain an alcohol-rich fraction, a low-boiler fraction and a high-boiler fraction.

8. The process according to claim 1, wherein the thermal separation unit comprises a thin film evaporator and a falling film evaporator, the thin film evaporator and the falling film evaporator being serially interconnected, optionally with the thin film evaporator being serially connected downstream of the falling film evaporator.

9. The process according to claim 1, wherein the thermal separation unit comprises two or three serially interconnected falling film evaporators.

10. The process according to claim 1, wherein the first membrane separation unit takes a form of a two-stage depleting cascade.

11. The process according to claim 1, wherein the catalyst system comprises a rhodium catalyst comprising an organophosphorus ligand, the ligand being selected from the group consisting of a phosphite, a phosphine and a phosphoramidite.

12. The process according to claim 1, wherein the olefin comprises eight carbon atoms and is hydroformylated to the aldehyde comprising nine carbon atoms, and the aldehyde is hydrogenated to an alcohol comprising nine carbon atoms.

13. A plant, comprising:
a) at least one hydroformylation reactor comprising a reactant inlet and a product outlet;

b) a first membrane separation unit comprising a first membrane entry point, a first permeate connection point and a first retentate connection point;

c) a thermal separation unit comprising a product inlet, a head product connection point and a bottom product connection point;

d) a second membrane separation unit comprising a second membrane entry point, a second permeate connection point and a second retentate connection point;

e) at least one hydrogenation reactor comprising an aldehyde entry point and an alcohol exit point;
wherein
the product outlet of the hydroformylation reactor connects directly or via a devolatilizer to the first membrane entry point of the first membrane separation unit;
the first retentate connection point of the first membrane separation unit connects to the reactant inlet of the hydroformylation reactor;
the first permeate connection point of the first membrane separation unit connects directly or via a devolatilizer to the product inlet of the thermal separation unit;
the bottom product connection point of the thermal separation unit connects to the second membrane entry point of the second membrane separation unit;
the head product connection point of the thermal separation unit connects directly or via an adsorber to the aldehyde entry point of the hydrogenation reactor;
the second retentate connection point of the second membrane separation unit connects together with the product outlet of the hydroformylation reactor to the first entry point of the first membrane separation unit;
the second permeate connection point of the second membrane separation unit connects directly or via the adsorber to the aldehyde entry point of the hydrogenation reactor; and
the second membrane separation unit takes a form of a two-stage enriching cascade.

14. The process according to claim 1, which is carried out in a plant comprising:
a) the at least one hydroformylation reactor comprising a reactant inlet and a product outlet;
b) the first membrane separation unit comprising a first membrane entry point, a first permeate connection point and a first retentate connection point;
c) the thermal separation unit comprising a product inlet, a head product connection point and a bottom product connection point;
d) the second membrane separation unit comprising a second membrane entry point, a second permeate connection point and a second retentate connection point;
e) at least one hydrogenation reactor comprising an aldehyde entry point and an alcohol exit point;
wherein
the product outlet of the hydroformylation reactor connects directly or via a devolatilizer to the first membrane entry point of the first membrane separation unit;
the first retentate connection point of the first membrane separation unit connects to the reactant inlet of the hydroformylation reactor;

the first permeate connection point of the first membrane separation unit connects directly or via a devolatilizer to the product inlet of the thermal separation unit;

the bottom product connection point of the thermal separation unit connects to the second membrane entry point of the second membrane separation unit;

the head product connection point of the thermal separation unit connects directly or via an adsorber to the aldehyde entry point of the hydrogenation reactor;

the second retentate connection point of the second membrane separation unit connects together with the product outlet of the hydroformylation reactor to the first entry point of the first membrane separation unit; and the second permeate connection point of the second membrane separation unit connects directly or via the adsorber to the aldehyde entry point of the hydrogenation reactor.

* * * * *